(12) United States Patent
Eriksson et al.

(10) Patent No.: US 6,446,010 B1
(45) Date of Patent: Sep. 3, 2002

(54) METHOD FOR ASSESSING SIGNIFICANCE OF PROTEIN IDENTIFICATION

(75) Inventors: Jan Eriksson, Uppsala (SE); David Fenyö; Brian T. Chait, both of New York, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 09/333,726

(22) Filed: Jun. 15, 1999

(51) Int. Cl.⁷ .............................................. G06F 19/00

(52) U.S. Cl. ...................................................... 702/19

(58) Field of Search ........................................ 702/19

(56) References Cited

U.S. PATENT DOCUMENTS 5,538,837 A 7/1996 Yates, III et al.

OTHER PUBLICATIONS

Henzel W.J., Billeci T.M., Stultz J.T., Wong S. C., Grimley C., and Watanbe C., "Identifying Proteins from two–dimensional gels by Molecular Mass Searching of Peptide Fragments in Protein Sequence Databases," *Proc. Natl. Acad. Sci. (USA)* 1993, 90, 5011–5015.

Mann M., Hojrup P., and Roepstorff P., "Use of Mass Spectrometric Molecular Weight Information to Identify Proteins in Sequence Databases," *Biol. Mass Spectrom.* 1993, 22, 388–345.

Pappin D.J.C., Hojrup P., and Bleasby A.J., "Rapid Identification of Proteins by Peptide–Mass Fingerprinting," *Current Biol.* 1993, 3, 327–332.

Yates J.R., III, Speicher S., Griffin P.R., and Hunkapiller T., "Peptide Mass Maps: A Highly Informative Approach to Protein Identification," *Anal. Biochem.* 1993, 214, 397–408.

James P, Quadroni M, Carafoli E, Gonnet G., "Protein Identification by Mass Profile Fingerprinting," *Biochem. and Biophys. Res. Commun.* 1993, 195, 58–64.

Mortz E., Vorm O., Mann M., Roepstorff P., "Identification of Proteins in Polyacrylamide Gels by Mass Spectrometric Peptide Mapping Combined with Database Search," *Biol. Mass Spectrom.* 1994, 23, 249–261.

James P, Quadroni M, Carafoli E, Gonet G., "Protein Identification in DNA databases by Peptide Mass Fingerprinting," *Protein Sci.* 1994, 3, 1347–1350.

Cottrell J.S., "Protein Identification by Peptide Mass Fingerprinting," *Peptide Research.* 1994, 3, 115–124.

Cordwell S.J., Wilkins M.R., Cerpa–Poljak A., Gooley A.A., Duncan M., Williams K.L., and Humprey–Smith I., "Cross–Species Identification of Proteins Separated by Two–Dimensional Gel Electrophoresis Using Matrix–Assisted Laser Desorption Ionisation/Time–Of–Flight Mass Spectrometry and Amino Acid Composition," *Electrophoresis.* 1995, 16, 438–443.

Jensen O.N., Podtelenikov A. V, Mann M., "Delayed Extraction Improves Specificity in Database Searches by Matrix–Assisted Laser Desorption/Ionization Peptide Maps," *Rap. Commun. Mass Spectrom.* 1996, 10, 1371–1378.

Jensen O.N., Vorm O., Mann M., "Sequence Patterns Produced by Incomplete Enzymatic Digestion or One–Step Edman Degradation of Peptide Mixtures as Probes For Protein Database Searches," *Electrophoresis.* 1996, 17, 938–944.

Courchesne P.L., Luethy R., Patterson S.D., "Comparison of In–Gel and On–Member Digestion Methods at Low to Sub–pmol Level for Subsequent Peptide and Fragment–Ion Mass Analysis Using Matrix–Assisted Laser–Desorption/Ionization Mass Spectrometry," *Electrophoresis.* 1997, 18, 369–381.

Zhang W., Chait B.T., "Protein Identification by Database Searching: A Bayesian Algorithm," Proceedings of the 43rd ASMS Conference on Mass Spectrometry and Allied Topics, Atlanta, Georgia, 1995, 643.

Eng J.K., McCormack A.L., Yates J.R., "An Approach to Correlate Tandem Mass Spectral Data of Peptides with Amino Acid Sequence in a Protein Database," *Amer. Soc. Mass Spec.* 1994, 5, 976–989.

Mann M. and Wilm M., "Error–Tolerant Identification of Peptides in Sequence Databases by Peptide Sequence Tags," *Anal. Chem.* 1994, 66, 4390–4399.

Yates J.R., Eng J.K., McCormack A.L., Schieltz D., "Method to Correlate Tandem Mass Spectra of Modified Peptides to Amino Acid Sequence in the Protein Database," *Anal. Chem.* 1995, 67, 1426–1436.

Yates J.R., Eng J.K., McCormack A.L., "Mining Genomes: Correlating Tandem Mass Spectra of Modified and Unmodified Peptides to Sequences in Nucleotide Databases," *Anal. Chem.* 1995, 67, 3202–3210.

Griffin P.R., MacCoss M.J., Eng J.K., Blevins R.A., Aaronson J.S., Yates J.R., "Direct Database Searching with MALDI–PSD Spectra of Peptides," *Rap. Commun. Mass Spec.* 1995, 9, 1546–1549.

Patterson, S.C., Aebersold, R., "Mass Spectrometric Approaches for the Identification of Gel–Separated Proteins," *Electrophoresis.* 1995, 16, 1791–1814.

Mortz E., O'Connor P., Roepstorff P., Kelleher N.L., Wood T.D., McLafferty F.W., Mann M., "Sequence Tag Identification of Intact Proteins by Matching Tandem Mass Spectral Data Against Sequence Data Bases," *Proc. Natl. Acad of Sci. (USA)* 1996, 93, 8264–8267.

(List continued on next page.)

Primary Examiner—John S. Brusca
(74) *Attorney, Agent, or Firm*—Hoffman & Baron, LLP; Irving N. Feit

(57) ABSTRACT

A method of generating a frequency distribution of scores comprising: a) generating mass data for a biological molecule; b) generating mass data for a series of random hypothetical biological molecules; c) calculating a frequency distribution of high similarity scores between mass data of each molecule generated in steps a and b.

67 Claims, 17 Drawing Sheets

OTHER PUBLICATIONS

Figeys D., Ducret A., Yates J.R., Aebersold R., "Protein Identification by Solid Phase Microextraction—Capillary Zone Electrophoresis—Microelectrospray—Tandem Mass Spectrometry," *Nature Biotechnology*. 1996, 14, 1579–1583.

McCormack A.L., Schieltz D.M., Goode B., Yang S., Barnes G., Drubin D., Yates J.R., III, "Direct Analysis and Identification of Proteins in Mixtures by LC/MS/MS and Database Searching at the Low–Femtomole Level," *Anal. Chem.* 1997, 69, 767–776.

Fenyö D., Qin J., Chait B.T., "Protein Identification Using Mass Spectrometric Information," *Electrophoresis*. 1998, 19, 998–1005.

Zhang W., Chait B.T., "ProFound—An Expert For Protein Identification," Proceedings of the 46th ASMS Conference on Mass Spectrometry and Allied Topics, Atlanta, Georgia, 1998, 969.

Yates J.R., "Database Searching Using Mass Spectrometry Data," *Electrophoresis*, 1998, 19, 893–900.

Fenyö D., Beavis R., "Network–Based Bioinformatics in Protein Mass Spectrometry," *Mass Spectrometry of Biological Materials*, Marcel Dekker, New York 1998, 435–460.

Clauser K.R., Baker P., Burlingame A.L., "Role of Accurate Mass Measurement (±10 ppm) in Protein Identification Strategies Employing MS or MS/MS and Database Searching," *Anal. Chem.* 1999, 71, 2871–2882.

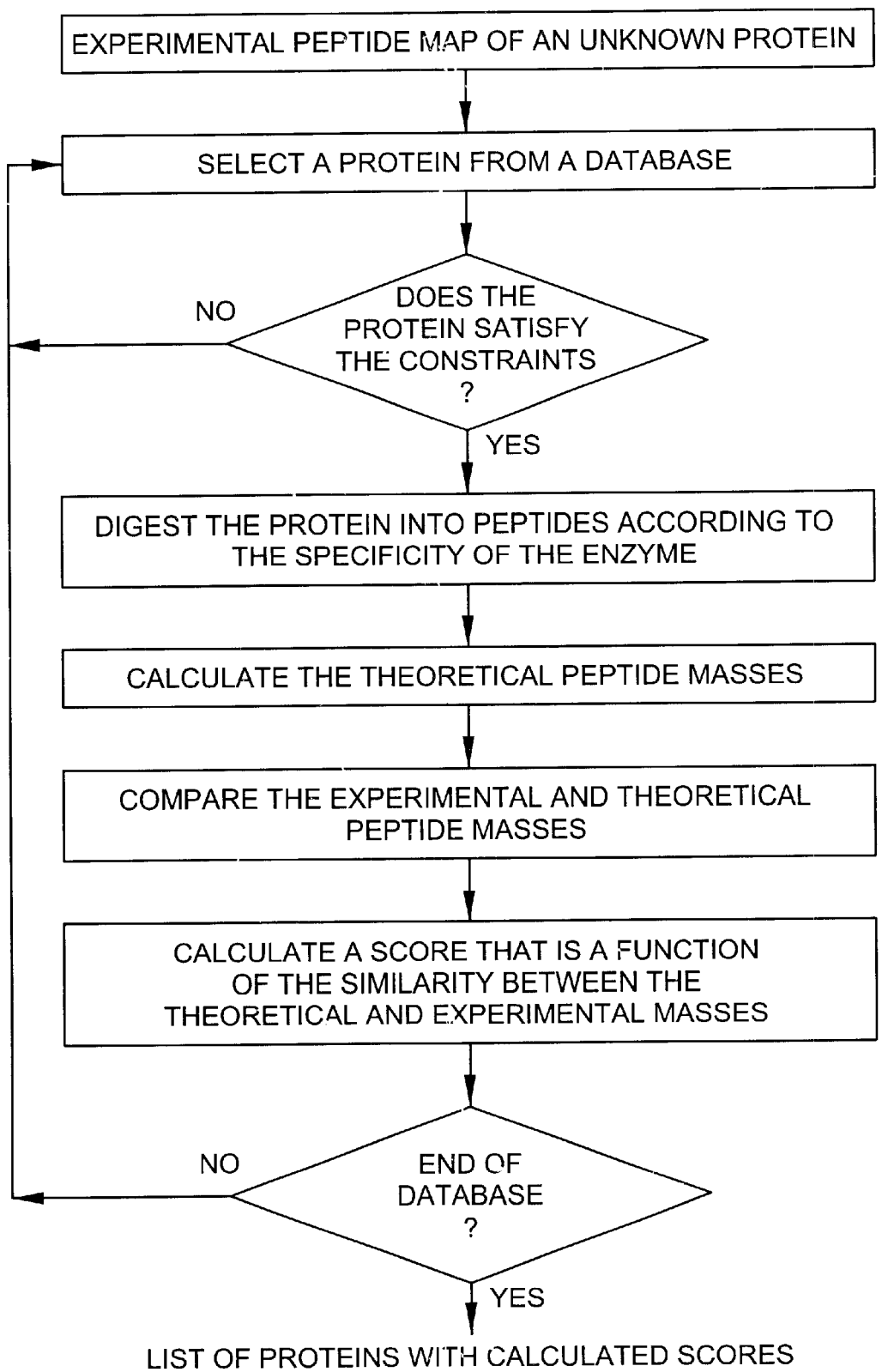
FIG. 8 PROTEIN IDENTIFICATION DATABASE SEARCH WITH INFORMATION FROM A PEPTIDE MAP FIG. 9 OBTAINING A SCORE FREQUENCY DISTRIBUTION
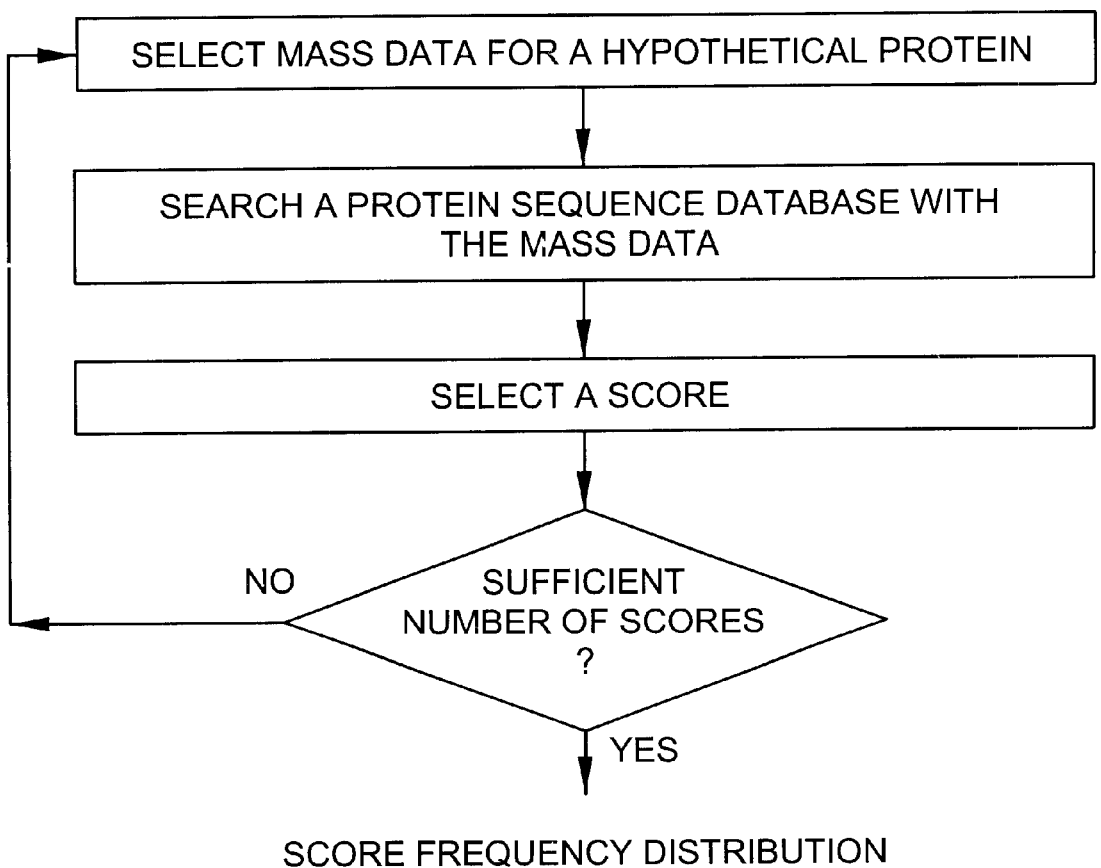

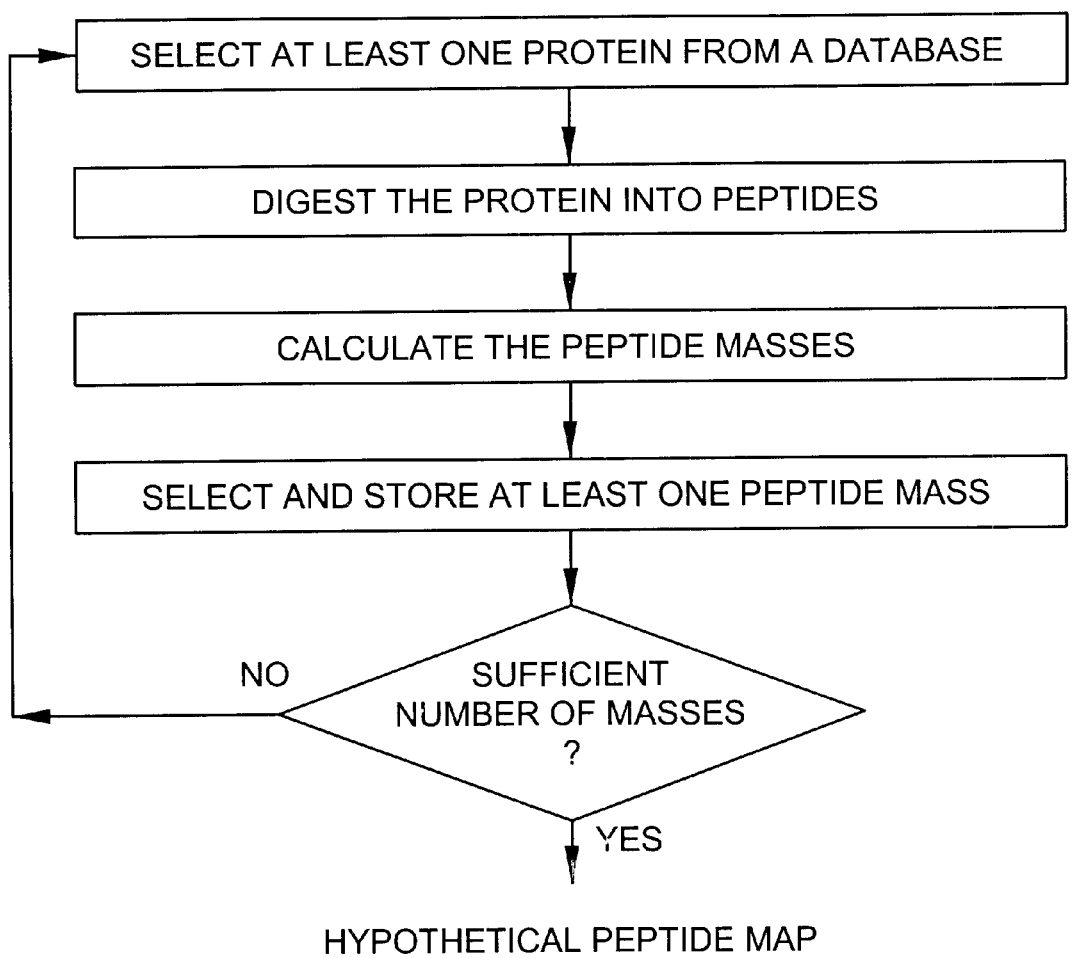
FIG. 10 GENERATION OF A HYPOTHETICAL PEPTIDE MAP

FIG. 11
PROTEIN IDENTIFICATION BY MS FRAGMENTATION
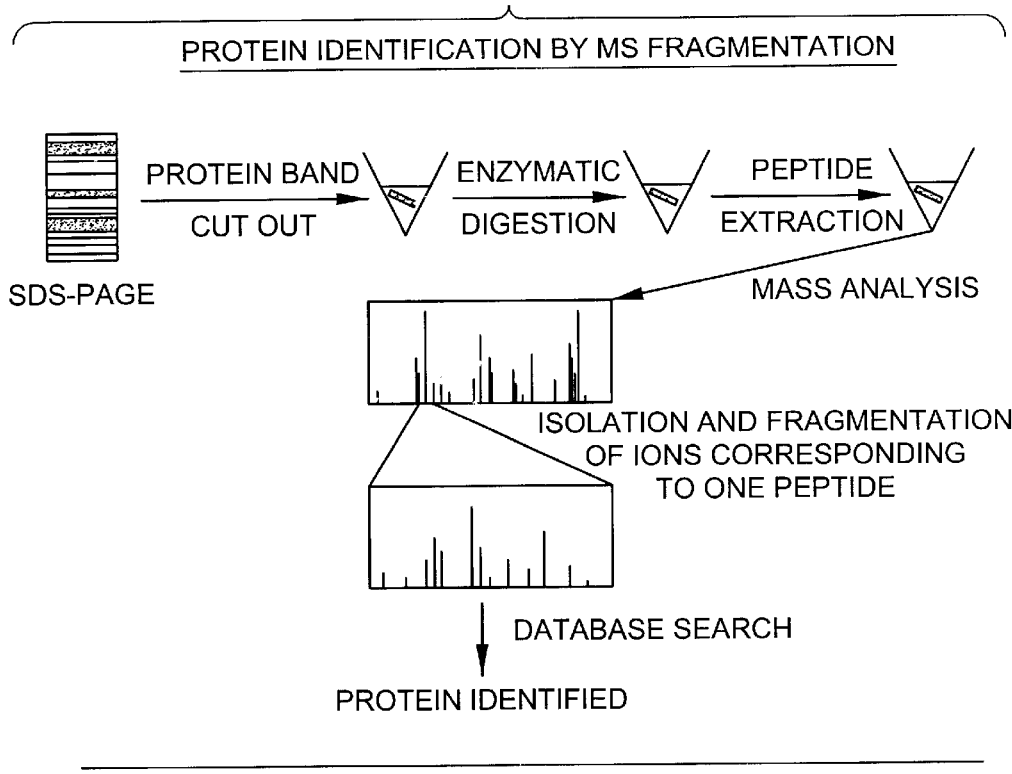
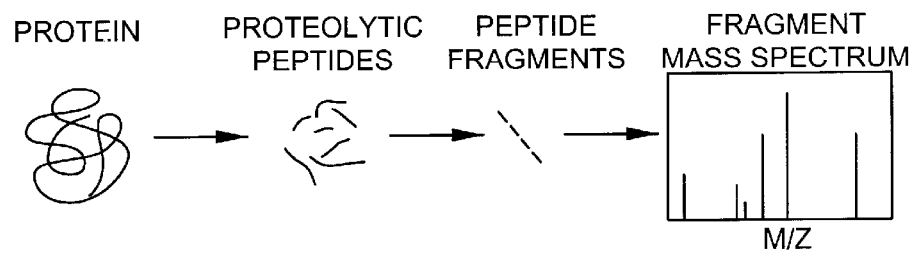
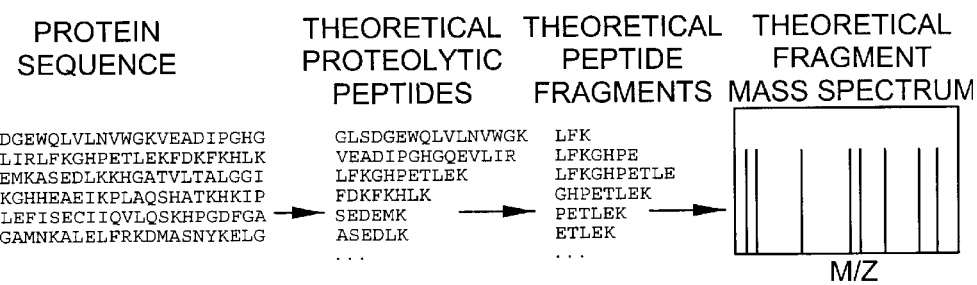

FIG. 12
PROTEIN IDENTIFICATION BY PEPTIDE MAPPING
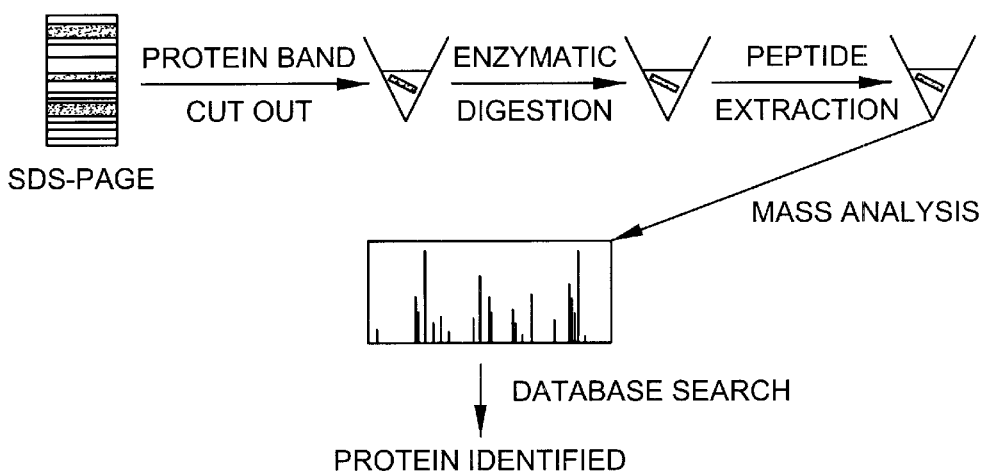
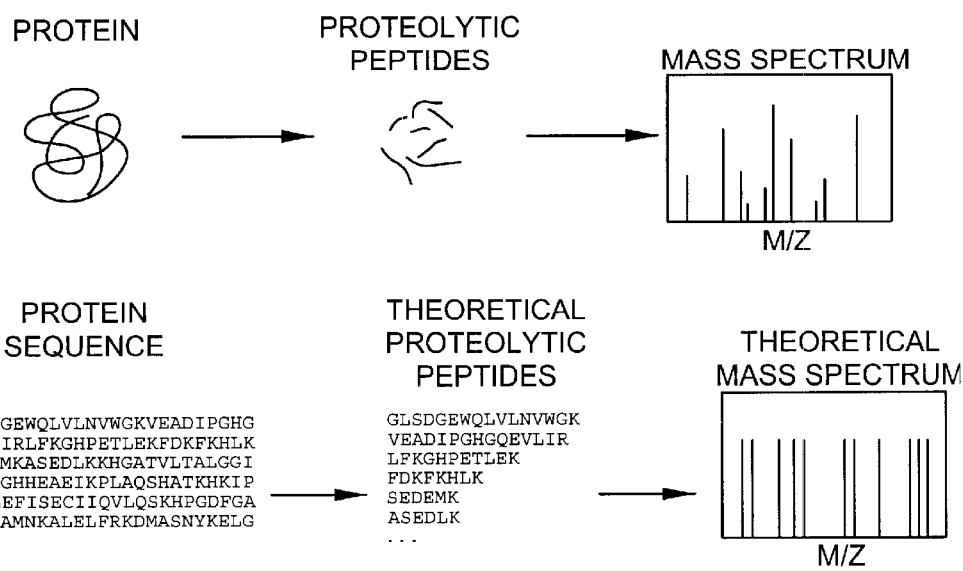

FIG. 13  FLOW CHART SHOWING THE STEPS IN A COMPLETE PROTEIN IDENTIFICATION MS/MS EXPERIMENT

METHOD FOR ASSESSING SIGNIFICANCE OF PROTEIN IDENTIFICATION

This work was supported by the following grant: RR00862 from the N.I.H. The government has certain rights to this invention.

BACKGROUND

An unknown biological molecule can be identified by comparing the mass data of the unknown biological molecule with mass data of known biological molecules.

For example, the rapid growth of available high quality DNA sequence data has made mass spectrometry (MS) combined with genome database searching a popular and potentially accurate method to identify proteins. Protein identification by mass spectrometry has proven to be a powerful tool to elucidate biological function and to find the composition of protein complexes and entire organelles.

In protein identification experiments, proteins are typically separated by gel electrophoresis, subjected to a protease having high digestion specificity (e.g. trypsin) and the resulting mixture of peptides is extracted from the gel and subjected to MS-analysis (1998). The distribution of proteolytic peptide masses (peptide map) is compared with theoretical proteolytical peptide masses calculated for each protein stored in a protein/DNA sequence database.

There are various algorithms that attempt to identify an unknown protein by determining the database protein which has a peptide map with the highest degree of similarity to the experimentally obtained peptide map of the unknown protein. These algorithms yield the protein identified and an identification score. Due to imperfections in the protein separation and to incomplete extraction of the proteolytic peptides from the gel, the peptide map is typically incomplete with respect to the protein identified, and also contains a background of proteolytic peptide masses from one or several other proteins. Even if separation and extraction were perfect, posttranslational modifications of proteins would cause a proteolytic peptide mass distribution to be different from that predicted by the genome. Mass spectrometry determines a peptide mass $m_i$ to an accuracy $\pm\Delta m_i$, with $\Delta m_i/m_i$ typically >30 ppm. Within the mass range $m_i \pm \Delta m_i$, proteolytic peptide masses of several proteins in the genome can match. For these reasons, a database search using the information in a peptide map will not always identify a protein unambiguously.

Despite the momentum mass spectrometric protein identification has given to protein research, the problem of objectively assessing the significance of a protein identification result has been overlooked. As increasingly complex biological problems are explored, knowledge of the significance of each protein identification result is likely to become critical.

The object of the present invention is to provide a method for assessing the significance of a biological molecule identification.

SUMMARY OF THE INVENTION

This and other objects, as will be apparent to those having ordinary skill in the art, have been met by providing a method of determining the statistical significance of a biological molecule identification score. The method comprises a) selecting a significance level that represents a level of confidence in a biological molecule identification b) calculating a score associated with an unknown biological molecule, wherein the score is a function of similarity between mass data of the unknown biological molecule and mass data generated for known biological molecules of a biological molecule database; c) comparing the score with a score frequency distribution, wherein the distribution is generated by comparing mass data of a hypothetical biological molecule with mass data generated for known biological molecules of a biological molecule database, and wherein the frequency distribution has associated therewith the significance level; and d) determining whether the score associated with the unknown biological molecule identification is within the significance level.

The invention further provides a method of generating a frequency distribution of scores for a particular experimental condition, wherein the scores relate to random identifications of biological molecules. The method comprises a) generating mass data for the particular experimental condition for known biological molecules in a biological molecule database; b) generating mass data of a hypothetical biological molecule for the experimental condition; c) comparing the data generated in step (b) with the data generated for each known biological molecule in step (a); d) calculating a score for each comparison in step (c), wherein the score is a function of similarity between the data generated in step (a) which corresponds to a particular known biological molecule and the data generated in step (b); e) selecting a score from the scores calculated in step (d), wherein the selected score corresponds to the comparison which denotes a high degree of similarity between the data generated in step (a) and the data generated in step (b); f) repeating steps (b) through (e) with different hypothetical biological molecules until a sufficient quantity of scores are selected; and g) determining the frequency of selecting each score and generating therefrom a frequency distribution of scores.

The invention provides another method of generating a frequency distribution of scores for a particular experimental condition, wherein the scores relate to random identifications of biological molecules. The method comprises a) generating mass data to for the particular experimental condition for known biological molecules in a biological molecule database; b) randomly selecting a biological molecule from the database; c) comparing the mass data of the randomly selected biological molecule with the mass data of each known biological molecule; d) calculating a score for each comparison in step (c), wherein the score is a function of similarity between the data; e) selecting a score from the scores calculated in step (d), wherein the selected score corresponds to the comparison which denotes a degree of similarity between the data which is lower than the highest degree of similarity; f) repeating steps (b) through (d) with different randomly selected biological molecules until a sufficient quantity of scores are selected; and g) determining the frequency of selecting each score and generating therefrom a frequency distribution of scores.

The invention also provides a method of identifying an unknown biological molecule for a particular experimental condition and a particular significance level. The method comprises a) selecting a significance level that represents a level of confidence in a biological molecule identification; b) cleaving the unknown biological molecule into constituent parts by a method that produces constituent parts; c) generating mass data for these constituent parts; d) comparing the mass data generated in step (c) with mass data generated for the experimental condition from known biological molecules of a biological molecule database; e) calculating scores for each comparison in step (d), wherein the scores are a function of similarity between mass data of the unknown biological molecule and mass data generated from the biological molecule database; f) selecting a score generated in step (e) wherein the score corresponds to a comparison which denotes a high degree of similarity and wherein the score corresponds to a particular known biological molecule in the biological molecule database; and g) determining whether the score selected in step (f) is equal to or larger than the critical score.

In another embodiment the invention comprises a computer program product which comprises a computer usable medium having computer readable program code means embodied in said medium for generating a frequency distribution of scores, wherein the scores relate to random identifications of biological molecules. The computer program product includes: a computer readable program code means for causing a computer to generate mass data for each known biological molecule in a biological molecule database for a particular experimental condition; computer readable program code means for causing the computer to generate mass data of a hypothetical biological molecule for the experimental condition; computer readable program code means for causing the computer to compare the mass data of the hypothetical biological molecule with the mass data generated for each known biological molecule in the biological molecule database for the particular experimental condition; computer readable program code means for causing the computer to calculate a score for each mass data comparison, wherein the score is a function of similarity between the mass data corresponding to a particular known biological molecule and the mass data corresponding to the hypothetical biological molecule; computer readable program code means for causing the computer to select a score from the calculated scores, wherein the selected score corresponds to the comparison which denotes a high degree of similarity between the mass data corresponding to the particular known biological molecule and the mass data corresponding to the hypothetical biological molecule; computer readable program code means for causing the computer to repeatedly generate mass data of different hypothetical biological molecules, compare the mass data each of the hypothetical molecules with the mass data generated for each known biological molecule in the biological molecule database, calculate a score for each of the mass data comparisons and select a score from the calculated scores until a sufficient quantity of scores are selected; and computer readable program code means for causing the computer to determine the frequency of selecting each score and to generate therefrom a frequency distribution of scores.

In another embodiment the invention comprises a computer program product which comprises a computer usable medium having computer readable program code means embodied in said medium for identifying an unknown biological molecule for a particular experimental condition and a particular significance level. The computer program product includes: computer readable program code means for causing a computer to generate mass data of an unknown biological molecule, the unknown biological molecule having been cleaved into constituent parts by a method that produces constituent parts; computer readable program code means for causing the computer to compare the mass data of the unknown biological molecule with mass data generated for the experimental condition from known biological molecules of a biological molecule database; computer readable program code means for causing the computer to calculate scores for each mass data comparison, wherein the scores are a function of similarity between mass data of the unknown biological molecule and mass data generated from the biological molecule database; computer readable program code means for causing the computer to select a score from the calculated scores, wherein the selected score corresponds to a particular known biological molecule in the biological molecule database, and wherein the selected score corresponds to a comparison which denotes a high degree of similarity; computer readable program code means for causing the computer to compare the selected score with a frequency distribution of scores for the experimental condition, wherein the distribution is generated by comparing mass data of a hypothetical biological molecule with mass data generated from a biological molecule database, and wherein the frequency distribution has associated therewith a critical score which corresponds to the significance level; and computer readable program code means for causing the computer to determine whether the selected score is equal to or larger than the critical score.

In another embodiment the invention comprises a computer program product which comprises a computer usable medium having computer readable program code means embodied in said medium for determining statistical significance of a biological molecule identification score. The computer program product includes: a computer readable program code means for causing a computer to calculate a score associated with an unknown biological molecule, wherein the score is a function of similarity between mass data of the unknown biological molecule and mass data generated from a biological molecule database; computer readable program code means for causing the computer to compare the score with a score frequency distribution, wherein the distribution is generated by comparing mass data of a hypothetical biological molecule with mass data generated from a biological molecule database, and wherein the frequency distribution has associated therewith a significance level determined to represent a confident biological molecule identification; and computer readable program code means for causing the computer to determine whether the score associated with the unknown biological molecule identification is within the significance level.

DESCRIPTION OF FIGURES

FIG. 8: Protein Identification Database Search with Information from a Peptide Map.

FIG. 9: Obtaining a Score Frequency Distribution.

FIG. 10: Generation of a Hypothetical Peptide Map.

FIG. 11: Protein Identification by MS Fragmentation.

FIG. 12: Protein Identification by Peptide Mapping.

DETAILED DESCRIPTION

Figure 1A:
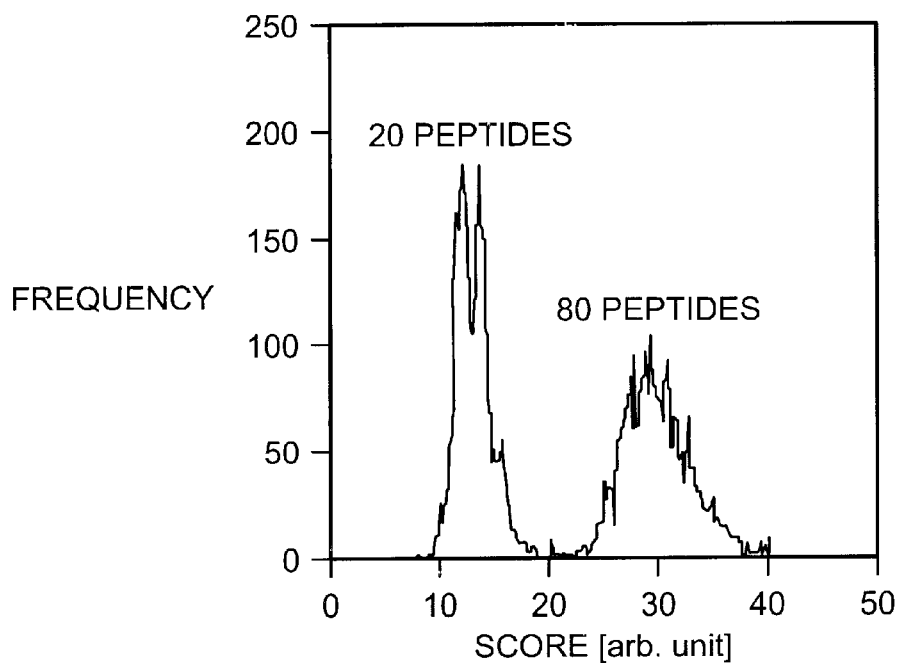
FIG. 1a: Score frequencies for proteins identified from 300 different random peptides maps composed of 20 and 80 tryptic peptide masses. Algorithm 1 was used to generate scores.

In one embodiment the invention provides a method of identifying an unknown biological molecule. Biological molecules include any biological polymer that can be degraded into constituent parts. The degradation is preferably into constituent parts at predictable positions to form predictable masses. Examples of biological molecules include proteins, nucleic acid molecules, polysaccharides and carbohydrates.

Proteins are polymers of amino acids. Constituent parts of proteins comprise one or more amino acids. A constituent part of a protein that contains more than one amino acid is referred to herein as a peptide.

Nucleic acids are polymers of nucleotides. Constituent parts of nucleic acids comprise one or more nucleotides. A constituent part of an nucleic acid that contains more than one nucleotide is referred to herein as an oligonucleotide.

Polysaccharides are polymers of monosaccharides. Constituent parts of polysaccharides comprise one or more monosaccharides. A constituent part of a polysaccharide that contains more than one monosaccharide is referred to herein as an oligosaccharide.

Mass data of biological molecules is quantifiable information about the masses of the constituent parts of the biological molecule. Mass data includes individual mass spectra and groups of mass spectra. The mass spectra can be in the form of peptide maps, oglionucleotide maps or oligosaccharide maps.

Mass data for proteins can be generated in any manner which provides mass data within a certain accuracy. Examples include matrix-assisted laser desorption/ionization mass spectrometry, electrospray ionization mass spectrometry, chromatography and electrophoresis. Mass data can also be generated by a general purpose computer configured by software or otherwise.

For the purposes of the present invention the mass data, for example a peptide mass, $m_i$, is determined to an accuracy $\pm \Delta m_i$, with $\Delta m_i/m_i$ preferably <10,000 ppm, more preferably <100 ppm and most preferably <30 ppm.

A step in generating mass data of a biological molecule may include first cleaving the biological molecule into constituent parts. Biological molecules may be cleaved by methods known in the art. Preferably, the biological molecules are cleaved into constituent parts at predictable positions to form predictable masses. Methods of cleaving include chemical degradation of the biological molecules. Biological molecules may be degraded by contacting the biological molecule with any chemical substance.

For example, proteins may be predictably degraded into peptides by means of cyanogen bromide and enzymes, such as trypsin, endoproteinase Asp-N, V8 protease, endoproteinase Arg-C, etc. Nucleic acids may be predictably degraded into constituent parts by means of restriction endonucleases, such as Eco RI, Sma I, BamH I, Hinc II, etc. Polysaccharides may be degraded into constituent parts by means of enzymes, such as maltase, amylase, alpha-mannosidase, etc.

The invention relates to improving current methods for identifying biological molecules by adding to current methods an assessment of the significance of the identification. Current methods for identifying biological molecules as well as the methods of the present invention will be described for protein identification. These methods are equally applicable to any biological molecule.

Current methods used to identify unknown proteins are typically similar to that illustrated in FIG. 12 but with the addition of database searching. The unknown protein is first cleaved into its constituent parts, as described above. The masses of the resulting constituent parts are analyzed and an experimental peptide map is generated. The determined masses are then compared against theoretical mass data generated for polypeptide sequences of a genome DNA (genome, cDNA, or otherwise) and/or protein database.

A biological molecule database is any compilation of information about characteristics of biological molecules. Databases are the preferred method for storing both polypeptide amino acid sequences and the nucleic acid sequences that code for these polypeptides. The databases come in a variety of different types that have advantages and disadvantages when viewed as the hypothesis for a polypeptide identification experiment. The properties of the most common databases currently in use are listed in Table 4.

While the "database entry" for an amino acid sequence may appear to be a simple text file to a user browsing for a particular polypeptide, many databases are organized into very flexible, complicated structures. The detailed implementation of the database on a particular system may be based on a collection of simple text files (a "flat-file" database), a collection of tables (a "relational" database), or it may be organized around concepts that stem from the idea of a protein, gene, or organism (an "object-oriented" database).

Protein mass data may be predicted from nucleic acid sequence databases. Alternatively, protein mass data may be obtained directly from protein sequence databases which contain a collection of amino acid sequences represented by a string of single-letter or three-letter codes for the residues in a polypeptide, starting at the N-terminus of the sequence. These codes may contain nonstandard characters to indicate ambiguity at a particular site (such as "B" indicating that the residue may be "D" (aspartic acid) or "N" (asparagine). The sequences typically have a unique number-letter combination associated with them that is used internally by the database to identify the sequence, usually referred to as the accession number for the sequence.

Databases may contain a combination of amino acid sequences, comments, literature references, and notes on known posttranslational modifications to the sequence. A database that contains these elements is referred to as "annotated." Annotated databases are used if some functional or structural information is known about the mature protein, as opposed to a sequence that is known only from the translation of a stretch of nucleic acid sequence. Non-annotated databases only contain the sequence, an accession number, and a descriptive title.

In general, each comparison of the unknown protein with a database protein is assigned a score on the basis of a reasonable algorithm. Algorithms, discussed below, exist that measure the probability that a particular sequence could give rise to the experimental results.

Comparisons can be made and scores can be generated by a general purpose computer configured by software or otherwise. The unknown protein is then "identified" with a sequence that produces a score having a high degree of similarity.

More specifically, a score is a measure of the degree of similarity between the theoretical mass data of a database protein and the measured (experimental) mass data of an unknown protein for the same experimental conditions. The experimental conditions under which an unknown protein and the proteins from the database are handled should be the same.

Experimental conditions include the manner in which cleavage of the proteins is accomplished, that is, the specific substance used for the chemical degradation of the proteins. Additionally, the experimental condition defines the efficiency of the chemical degradation. The efficiency of a chemical degradation specifies the number of potential cleavage sites which may be expected to remain uncleaved. The mass data generated from the protein database may include mass data representing proteins with incomplete cleavages. Experimental conditions also include the method by which the mass data is generated.

Scores which denote a high degree of similarity are the top twenty scores generated in a comparison, more preferably the top ten scores, even more preferably the top five scores and most preferably the top one score.

A similarity between a group of measured masses of the unknown protein and a group of theoretical masses of a database protein is assessed by comparing every measured mass with every theoretical mass. A simple algorithm for the measure of similarity is the number of measured masses that are similar to at least one theoretical mass. For example, a measured peptide map of an enzymatically digested unknown protein can be compared with the theoretical masses calculated by applying the rules for the specificity of the enzyme to the amino acid sequence of a database protein.

More sophisticated algorithms can be used to generate a score. For example, ProFound (ProteoMetrics) is a software tool for searching protein sequence databases which measures similarity using a Bayesian statistical framework.

In this invention a measured mass of an unknown protein and the theoretical mass of the protein of the database are said to similar if the absolute value of the difference between them is less than the uncertainty in the measurement.

The similarity between the mass data of the unknown protein and the theoretical mass data of the database proteins is assessed taking into account the accuracy of the determination of the mass data by a particular method. For example, mass spectrometry determines a peptide mass $m_i$ to an accuracy of $\pm \Delta m_i$, with $\Delta m_i/m_i$ typically >30 ppm.

Therefore, within the mass range $m_i \div \Delta m_i$ peptide masses of several proteins in the database are considered to match the unknown protein.

The observed molecular mass or the observed isoelectric point of a protein can be used in combination with the measured masses of peptides generated by proteolysis to constrain the search for a polypeptide. In particular, the comparison between the theoretical mass data of the database proteins and the mass data of the unknown protein may be constrained to only those proteins of the database which are within a chosen mass range. The chosen mass range is preferably within 50% of the mass of the unknown protein, more preferably within 35%, most preferably within 25%.

Similarly, the comparison between the theoretical mass data of the database proteins and the mass data of the unknown protein may be constrained to only those proteins of the database which are within a chosen isoelectric point range. The isoelectric point (pI) of a protein is the pH at which its net charge is zero. The chosen isoelectric point range is preferably within 50% of the isoelectric point of the unknown protein, more preferably within 35%, most preferably within 25%.

Using the observed molecular mass or isoelectric point of a polypeptide to constrain a search must be done carefully. When nonannotated nucleotide sequence databases are used (such as TREMBL or GENPEPT), subsequent processing can greatly alter the pI or molecular mass of a protein, so much so that no identification can be made. For example, the small, highly conserved protein ubiquitin (SWISSPROT accession number P02248) has a molecular mass of 8.6 kD, which is the mass that would be measured by a mass spectrometer or a gel. A simple keyword search of the translated-nucleotide database GENPEPT results in several sequences for the same protein [accession numbers M26880 (77 kD), U49869 (25.8 kD) and X63237 (17.9 kD)]. None of these nucleotide-translated sequences give the correct molecular mass or pI, so using those parameters to limit a search would result in missing the database sequence altogether. Only annotated databases that fully outline known modifications can be used when the properties of the mature protein are being used to constrain a search.

Biological molecules may undergo common modifications in their structure. The mass data which is generated from a biological molecule database may include mass data representing biological molecules with common modifications.

Examples of such modifications are posttranslational modifications of proteins. The modification state of a protein is usually not known in detail. In database searches, it can be useful to assume that some common modifications might be present. This is achieved by comparing the measured peptides masses of the unknown protein with both the masses of the unmodified and modified peptides in the database.

Examples of posttranslational modifications include glycosylation and the oxidation of the amino acid methionine. Another example is the phosphorylation of the amino acids serine, threonine, and tyrosine. Phosphorylation is often used to activate or deactivate proteins and the phosphorylation state of an experimentally observed protein depends on may factors including the phase of the cell cycle and environmental factors.

Optionally, further information of the unknown protein's sequence is obtained by generating fragment mass data. Fragment mass data for a peptide can be generated in any manner which provides fragment mass data within a certain accuracy. Experimental conditions include the type of energy used to generate the fragment mass data. Vibrational excitation energy can be used. The vibrational excitation may be generated by collisions of the peptide with electrons, photons, gas molecules or a surface. Electronic excitation can be used. The electronic excitation may be generated by collisions of the peptide with electrons, photons, gas molecules (e.g. argon) or a surface.

In another example, a measured fragment mass spectrum of a peptide from an enzymatically digested unknown protein is compared with the theoretical masses calculated by applying the rules for the specificity of the enzyme, and the rules for the fragmentation as known to those of ordinary skill in the art, to the amino acid sequence of a database protein. For example, the software tool PepFrag (ProteoMetrics) allows for searching protein or nucleotide sequence databases using a combination of mass spectra data and fragmentation mass spectra data.

Figure 13:
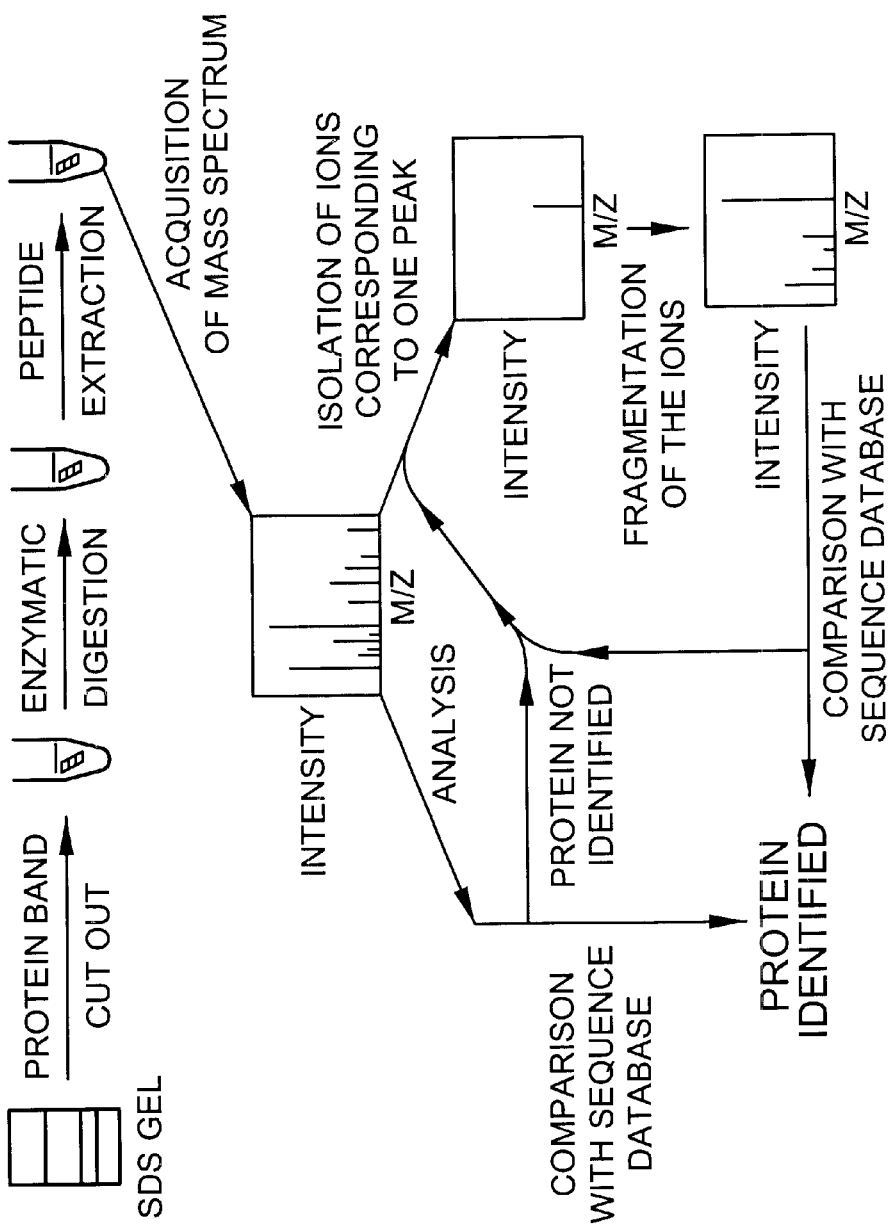
FIG. 13: Flow Chart Showing the Steps in a Complete Protein Identification MS/MS Experiment.

Fragment mass data for the purposes of this invention can be generated by using multidimensional mass spectrometry (MS/MS), also known as tandem mass spectrometry. A number of types of mass spectrometers can be used including a triple-quadruple mass spectrometer, a Fourier-transform cyclotron resonance mass spectrometer, a tandem time-of-flight mass spectrometer, and a quadruple ion trap mass spectrometer. FIG. 13 illustrates this type of experiment. A single peptide from a protein digest is subjected to MS/MS measurement and the observed pattern of fragment ions is compared to the patterns of fragment ions predicted from database sequences.

All of the protein identification strategies outlined above to generate a score are currently available as CGI programs that can be accessed using a browser. Table 3 is a list of the programs available, as well as some of the relevant characteristics of the programs.

There is a risk of false identification of the unknown protein for several reasons. For example, each proteolytic peptide mass measured can be found in several proteins in a genome database. Also for example, a peptide map is often incomplete with respect to the protein identified and can contain a background of proteolytic peptide masses from other proteins. An identification of a protein is definitely uncertain if the result is characterized by a score that could as well be due to random matching between the peptide map of the unknown protein and a protein in the database.

This invention provides a method of assessing the statistical significance of a protein identification score for a particular experimental condition. The method comprises generating a frequency distribution describing the null hypothesis ($H_0$). In the present specification, $H_0$ is defined as: "a protein identification is random and false."

A score frequency distribution for random protein identifications describes this null hypothesis. (For example see FIG. 14) A significance level ($\alpha$) is chosen which represents the level of confidence desired for a particular protein identification. This significance level, along with the corresponding critical score ($S_C$), is indicated on the frequency distribution. A protein identification score is then compared to the frequency distribution. If the score falls within the significance level ($\alpha$), the null hypothesis is rejected. The alternate hypothesis, "a protein identification is nonrandom," is then accepted. In other words, the null hypothesis should be rejected if the protein identification score is equal to or larger than the critical score since the critical score corresponds to the significance level.

The significance level of a protein identification result gives, in contrast with the identification score, an objective view of the quality of the result. However, significance testing can never tell if a result is true or false. Only biological methods have the potential of showing if a protein identification result is true.

The frequency of false results for repeated protein identifications using real data and significance testing at α level a is not generally predictable. The relative frequency of false results depends on the data as well as on the significance level chosen. A significant result is either false or true, as is a non-significant result. However, a general feature of significance testing is that if the significance level, α, is decreased, the relative frequency of false results considered to be significant is expected to decrease, and the relative frequency of true results considered non-significant is expected to increase. Optimized protein identification would, therefore, require (1) the use of an identification algorithm that maximizes the relative frequency of true identifications, and (2) the use of significance testing at an appropriate significance level to discriminate against false identifications. Significance testing has the potential to reduce the relative frequency of false identifications independently of the identification algorithm used.

In one embodiment the invention provides a method of generating a frequency distribution of scores for a particular experimental condition, wherein the scores relate to random identifications of proteins.

A frequency distribution is any compilation of the observed values of the variable being studied and how many times each value is observed. Frequency distributions can be in the form of a table of listings, a bar graph, a histogram, a frequency polygon, or a continuous curve. Functions derived from frequency distributions can be continuous (probability density function) or discrete (probability mass functions). Cumulative distribution functions of each type of function can also be derived.

The method comprises generating mass data for the particular experimental condition for known proteins from a protein sequence database as described above.

Mass data of a hypothetical protein for the same experimental condition is also generated. A hypothetical protein is any protein which is generated from selected peptides. These peptides may be selected from proteins which are selected from a database of proteins. These proteins and peptides may be selected by any method of selection. Selection may be accomplished by randomly selecting peptides from randomly selected proteins of a protein sequence database. (See Trypticm Peptide Maps in the Example below.) Additionally, selection may be accomplished by selecting preselected peptides, such as the second peptides, of the selected proteins. Further selection may be limited to selecting the protein within a chosen mass range. The selected mass range may be from about 0.1 to about 300 kDa.

A sufficient number of peptides selected to generate a hypothetical protein may be in the range of about 1 to about 1000, more preferably from about 10 to 100.

Hypothetical proteins are preferably generated in such a manner that the set of peptides comprising the hypothetical proteins is different from every set of peptides of the proteins in the database. Hypothetical proteins can be generated by a general purpose computer configured by software or otherwise.

Hypothetical proteins can also be generated by a mass spectrometer. A complicated mixture of proteins is enzymatically digested. Mass data is generated for these proteins.

The mass data, and optionally fragment mass data, generated for the hypothetical protein is compared with the data generated for each known protein in the database. The comparisons are carried out as described above. Since comparisons are made with a hypothetical protein, protein identifications are considered to be false and random. A score is calculated for each comparison. A score or scores are selected which correspond to the comparison denoting a high degree of similarity between the data. Additional and different hypothetical biological molecules are generated and comparisons performed until a sufficient quantity of scores are selected. A sufficient quantity of scores may, for example, be in the range of about 1 to $10^{10}$ scores, preferably 10 to $10^8$, more preferably 50 to $10^9$ and most preferably from about 100 to about $10^7$. The frequency of selecting each score is determined from which a score frequency distribution for random protein identifications is generated.

This invention provides a second method by which to generate a score frequency distribution for random protein identifications. Mass data of a randomly selected protein are generated. In contrast to the hypothetical protein described above, which comprises peptides from different proteins, the randomly selected protein comprises a set of peptides from a single protein. The randomly selected protein is compared with database proteins and scores are calculated, as described above. The score which denotes a preselected degree of similarity, excluding the highest degree of similarity, between the randomly selected protein and a database protein is selected. An example is the score which denotes the second highest degree of similarity. Mass data of additional and different randomly selected proteins are generated and comparisons performed until a sufficient quantity of scores, as defined above, is selected. The frequency of selecting each score is determined from which a score frequency distribution for random protein identifications is generated.

Figure 14:
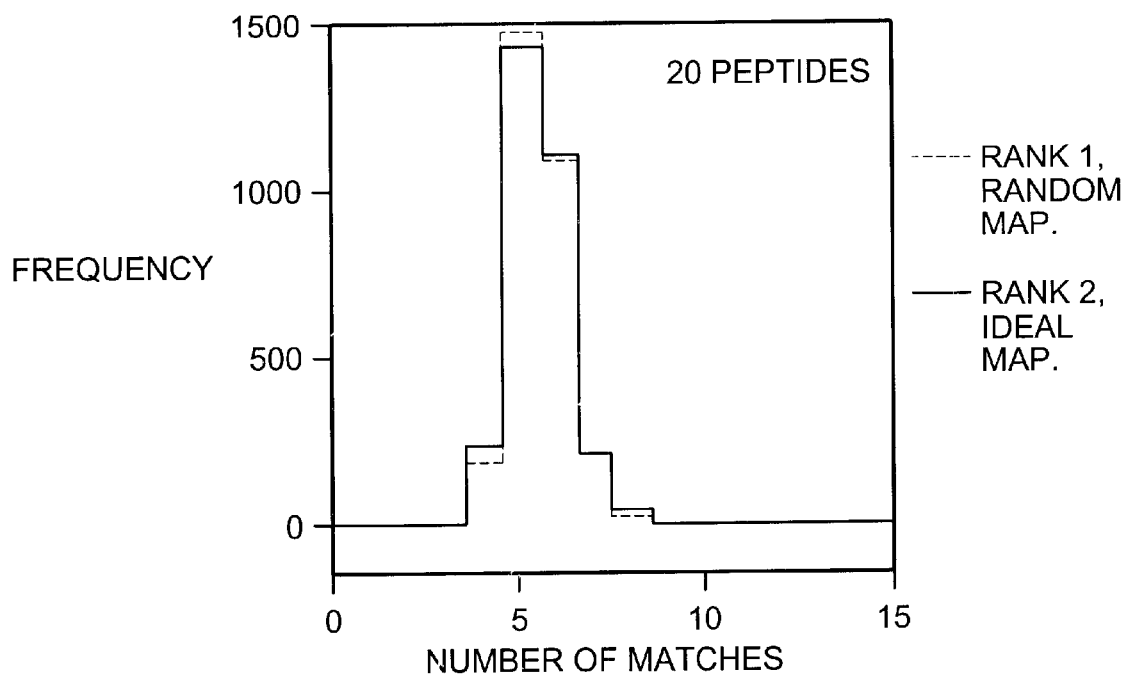
FIG. 14: Score distributions due to random matching from two different simulation models and algorithm 2. Similar results are obtained for the highest ranked protein when using random tryptic peptide maps (each mass from a different protein) as for the second highest ranked protein when using ideal tryptic peptide maps (all masses from a single protein). The latter method fails for large peptide maps.

As seen from FIG. 14, this second method yields a score frequency distribution which is very similar to the score frequency distribution generated by selecting the highest ranked protein identified on the basis of hypothetical proteins comprising maps with 20 tryptic peptides. If the size of the map is significantly greater than 20, only high-mass proteins could be the randomly selected proteins used in the second method (maximum number of tryptic peptides≈protein mass [Da]/1500 [Da]). These high-mass proteins have low abundance in the genome. The number of different maps available for large maps is therefore very limited, which would obscure the statistics in the score distribution for random matching.

In another embodiment the invention provides a method of determining the statistical significance of a protein identification score.

A significance level is selected which represents a level of confidence in a protein identification. The significance level is a function of a number of parameters, such as the number of masses in the peptide map, the mass accuracy, the degree of incomplete enzymatic cleavage, the protein mass range, and the size of the genome. The Examples below illustrate the influence of these parameters on the score required for a fixed significance level.

The significance level may, for example, be any value in the range from about from 0.0001 to about 0.1, more preferably in the range from about 0.001 to about 0.05.

A identification score for an unknown protein is calculated. The score is a function of similarity between mass data of the unknown biological molecule and mass data generated for known biological molecules of a biological molecule database. The score is compared with a frequency distribution of random protein identification scores. The frequency distribution indicates the selected significance level. It is determined whether the score associated with the unknown biological molecule identification is within the significance level. If the score is within the significance level, the null hypothesis is rejected, and the identification is considered significant within the selected significance level.

In another embodiment the invention provides a method of identifying an unknown protein for a particular experimental condition and a particular significance level. The unknown protein can be in a mixture of proteins.

A significance level that would indicate a confident biological molecule identification is chosen; the unknown protein is cleaved into constituent parts; mass data is generated for these constituent parts; the mass data is compared with mass data generated for the experimental condition from known proteins in a protein database; scores are calculated; and a score is selected, all as described above. The selected score is compared with the frequency distribution described above. The frequency distribution indicates the chosen significance level along with the corresponding critical score. It is determined whether the selected score is equal to or larger than the critical score on the frequency distribution. If the score for the identification of the unknown protein is greater than or equal to the critical score then the null hypothesis, that the protein identification is random and false, is rejected.

If significant protein identification is not achieved directly by the methods described above, a researcher can try to obtain additional, further constraining information by tandem mass spectrometry that utilizes fragmentation of the proteolytic peptide ions in the mass spectrometer followed by analysis of the distribution of fragment ion masses and database searching. Results obtained from this technique should also be subjected to significance testing once a statistical basis has been founded by simulation.

Frequency functions and the score required for various significance levels for a variety of experimental constraints and for two different identification algorithms have been estimated. (See Examples.) With the critical score, $S_C$, known for a variety of experimental constraints, this invention provides significance testing which is fully automated and integrated with database searching software used for protein identification. This is a general method that will ultimately remove the difficulties associated with different algorithms yielding different scores.

It is to be appreciated that the methods or algorithms of the present invention described herein above may be performed using a general purpose computer or processing system which is capable of running application software programs, such as an IBM personal computer (PC) or suitable equivalent thereof. Preferably, the application program code is embedded in a computer readable medium, such as a floppy disk or computer compact disk (CD). Furthermore, the computer readable medium may be in the form of a hard disk or memory (e.g., random access memory or read only memory) included in the general purpose computer.

As appreciated by one skilled in the art, the computer software code may be written, using any suitable programming language, for example, C or Pascal, to configure the computer to perform the methods of the present invention. While it is preferred that a computer program be used to accomplish any of the methods of the present invention, it is similarly contemplated that the computer may be utilized to perform only a certain specific step or task in an overall method, as determined by the user.

Preferably, the methods of the present invention are used with one or more displays (e.g., conventional CRT or liquid crystal display) provided with the processing system for presenting an indication of, for example, the final result of the process or algorithm. The display may preferably be utilized to present such information graphically (e.g., charts or three dimensional models of biological molecules) for further clarity.

In addition to performing the necessary calculations and processing functions in accordance with the present invention, the general purpose computer may also be used, for example, to store data pertaining to known biological molecules corresponding to a predetermined experimental condition. Such information may be stored on a hard disk or other memory, either volatile or non-volatile, included in the computer. Similarly, the information may be stored on a computer readable medium, such as floppy disk or CD, which can be transported for use on another computer system, as appreciated by those skilled in the art. In this manner, the methods of the present invention may be performed on any suitable general purpose computer and are not limited to a dedicated system.

Those of ordinary skill in the art will recognize that the present invention has wide applicability for identification of unknown biological molecules. Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the present invention.

EXAMPLES

Basic Protein Identification

A MALDI ion trap mass spectrometry (ITMS) spectrum of a tryptic digest of an unknown protein from *Saccharomyces cerevisiae* that was observed as a spot on a gel was generated. The spectrum has more than a dozen major peaks. If the corresponding masses are used t o search all *S. cerevisiae* sequences in OWL with ProFound, a list of proteins that are most likely to give the observed tryptic map is obtained (Table 2). In this example, submit P130 of eukaryotic initiation factor 4F (IF42__YEAST) is the most probable protein. To further increase the confidence in the identification, the ions with m/z=2596 were isolated and fragmented. The spectrum contains three major fragment ions. The peak at m/z=2468 is loss of the C-terminal lysine and contains little information. The two other fragment peaks, on the other hand, correspond to fragmentation at the C-terminal side of acidic amino acids. If a database is searched for proteins that have tryptic peptides with mass 2595 Da that fragment at the C-terminal side of acidic amino acids to give rise to b or y ions with mass 1984 and 2337 Da there is only one yeast protein (IF42__YEAST) in the public databases that agree with this information. The tryptic peptide is AQPISDIYEFAYPENVERPDIK and the two fragment ions correspond to fragment ion on the C-terminal side of the aspartic acids at residues 6 and 20, respectively. If a theoretical trypsin digest of IF42__YEAST is compared with the peptide map, all major peaks can be assigned to tryptic peptides from IF42__YEAST or to peptides from autolysis of trypsin.

Generation of a Hypothetical Protein and Significance Testing

Materials and Methods

The method designed to estimate frequency functions for random protein identification involves two steps: (1) generation of random peptide maps from a genome and (2) simulation of protein identification by searching a genome database and using the random peptide maps as data.

For the following experiments proteins were digested with trypsin. However, the significance testing method can be generalized to any protein identification experiment. The simulations can be generalized to all reasonable alternatives of proteases as well as tandem mass spectrometry.

Tryptic Peptide Maps

Random tryptic peptide maps (trypsin cleaves with high specificity at the carboxyl side of lysine and arginine) were generated from tryptic peptide masses predicted by the open reading frames (ORF:s) of a genome database. Each tryptic peptide mass was randomly chosen from a single randomly chosen protein in the database. Each protein was not allowed to contribute with more than one peptide mass to a particular map. Typically only completely digested tryptic peptides were used, but also maps with various degrees of incomplete cleavage in the tryptic peptides were used for comparison. Various data sets of random tryptic peptide maps were generated. Within each data set, all maps contained the same number (in the range 6–80) of tryptic peptide masses.

The genome databases used were: *Haemophilus influenzae, Saccharomyces cerevisiae,* and *Caenorhabditis elegans,* containing 1,718, 6,403, and 16,332 ORF:s respectively. *S. cerevisiae* was used predominantly and the other two databases only to study the influence of the size of the genome on the score distribution for random protein identification.

Simulation of Protein Identification Due to Random Matching

Each map of a data set was subjected to protein identification by database searching. Two different identification algorithms were employed that will be referred to as algorithm 1 and algorithm 2. Algorithm 1 is a streamlined version the ProFound algorithm (publicly available through the World Wide Web, http://prowl), which ranks the proteins according to a Bayesian likelihood calculated as the peptide map is compared with the database proteins. Algorithm 1 takes into account the number of matches between a database protein and the peptide map within the accuracy of the mass measurement, but also weighs in indirectly the protein mass as well as the expected efficiency of the protease used in an experiment. Algorithm 2 ranks proteins only according to their number of matches with tryptic peptide masses in the peptide map. In the simulations, the score and the name of the highest ranked protein as well as the source protein of each random tryptic peptide mass were stored for each random tryptic peptide map of a data set. Random and true identifications and random and false identifications could be distinguished. If more than one protein was identified and their sequences were not similar, the result was interpreted as false. A simulation with a set of different random peptide maps of the same size yields a distribution of the score for random protein identifications characteristic for that peptide map size and other constraints used in the database search. The typical parameters used in the simulations are summarized in Table 1. However, the experimentally pertinent parameters were varied systematically, one by one, in order to measure their respective influence on the identification score distribution.

The code for generating peptide maps as well as for the simulation of protein identification was written in C. A script written in Perl was employed for processing of the simulation results. All simulations were performed on a Dell XPS (300 MHZ Pentium Pro) personal computer.

Significance Testing

Figure 1B:
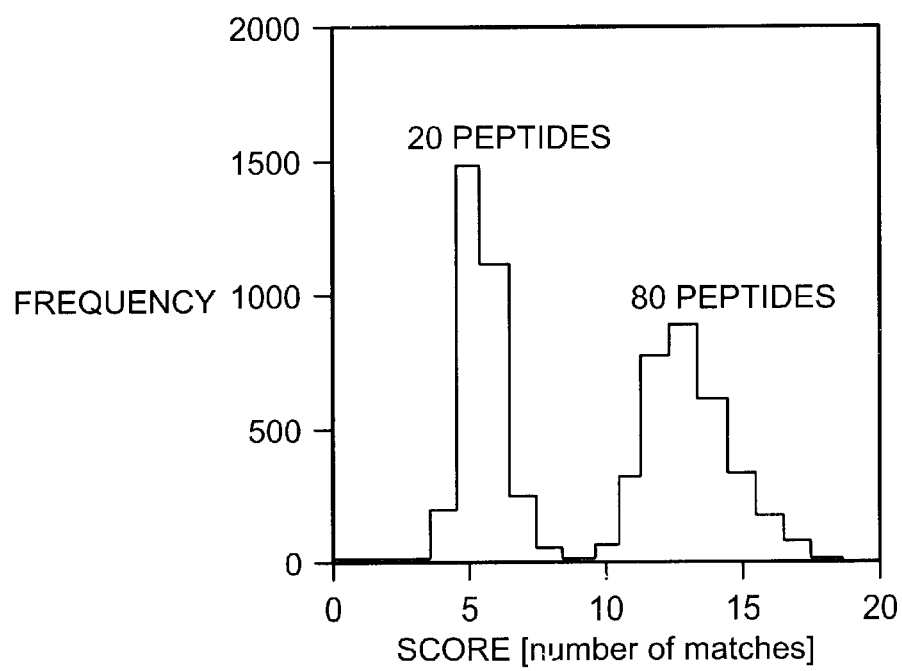
FIG. 1b: Score frequencies for proteins identified from 300 different random peptides maps composed of 20 and 80 tryptic peptide masses. Algorithm 2 was used to generate scores.
Figure 2A:
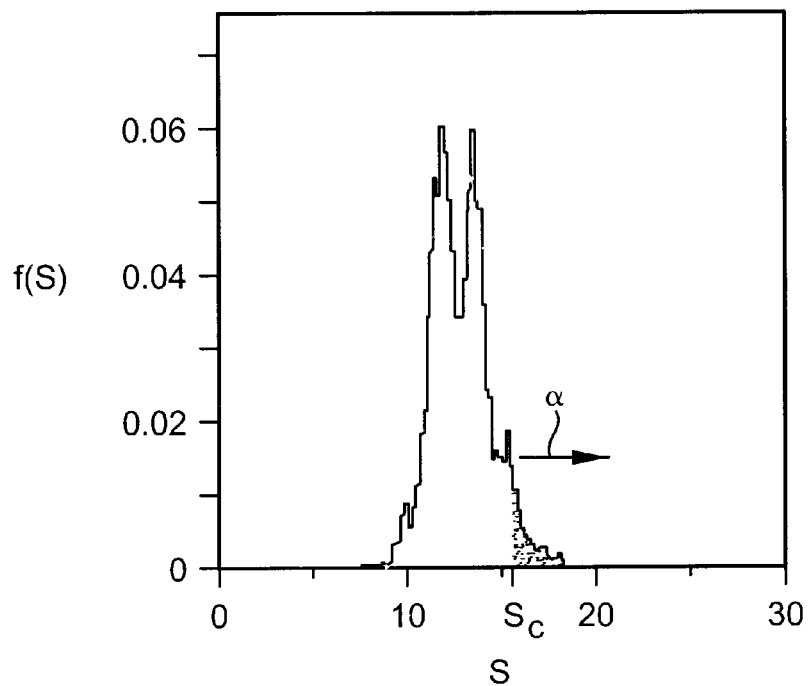
FIG. 2a: Frequency function f(S) for Algorithm 1 assumed to describe the null hypothesis $H_0$ "the protein identification is random and false." The area $\alpha$ of the shaded region under f(S> and $=S_C$) represents the probability that a result for which $H_0$ is true has at least the score $S_C$. In significance testing a is called the significance level.
Figure 2B:
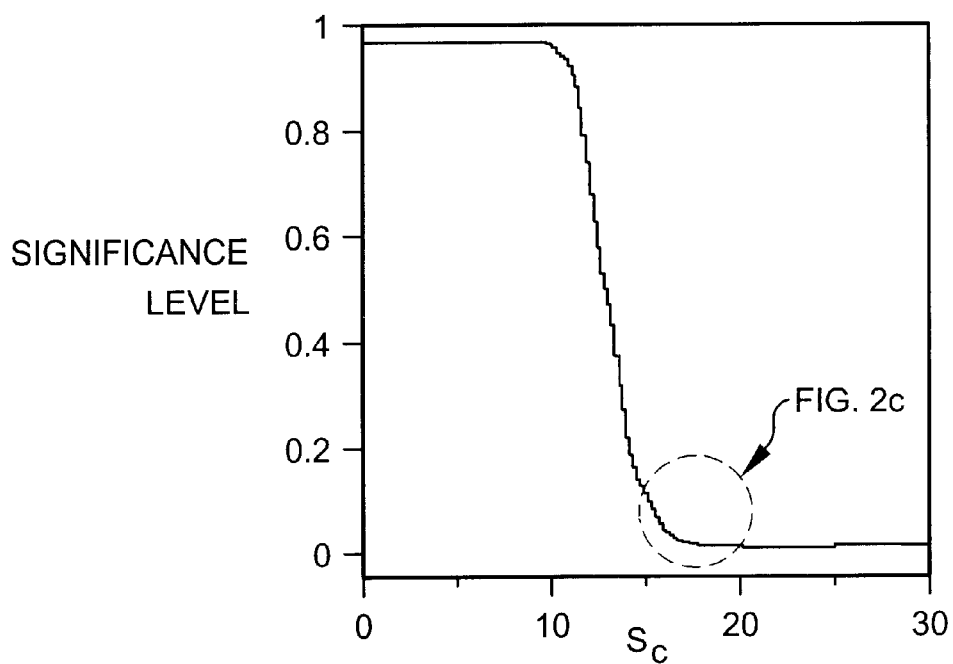
FIG. 2b: The significance level of FIG. 2a is shown as a function of $S_C$.
Figure 2C:
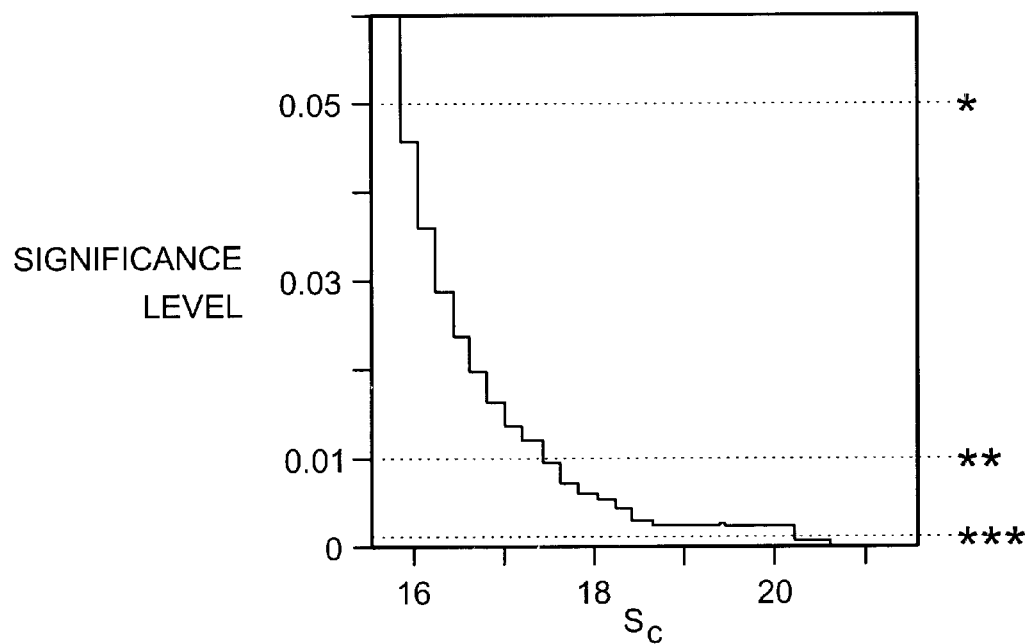
FIG. 2c: Magnified portion of FIG. 2b with horizontal lines indicating the significance levels: 0.05 (*), 0.01 () and 0.001 (*).
Figure 2D:
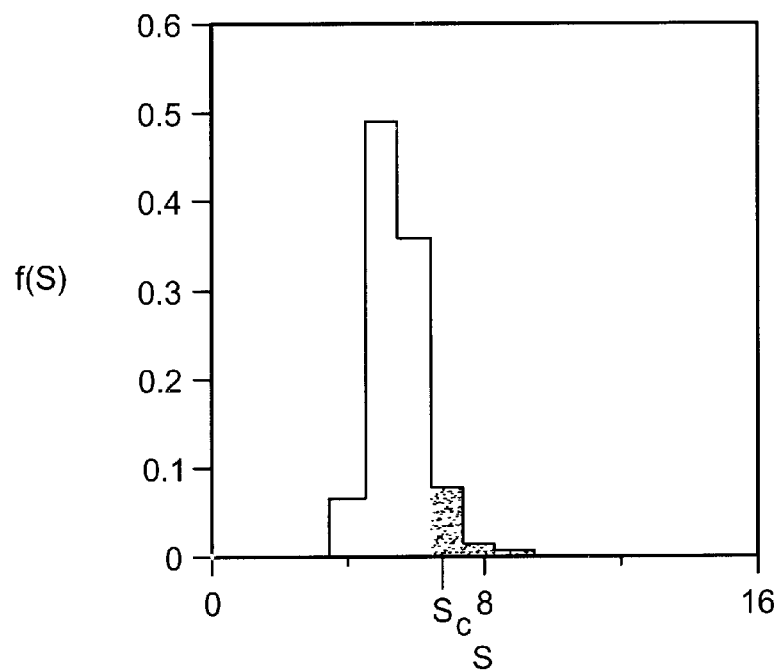
FIG. 2d: Parallels FIG. 2a, but with protein identification based on Algorithm 2. The better resolution of the score variable in algorithm 1 makes it easier to determine accurately the score $S_C$ that corresponds to a chosen $\alpha$.
Figure 2E:
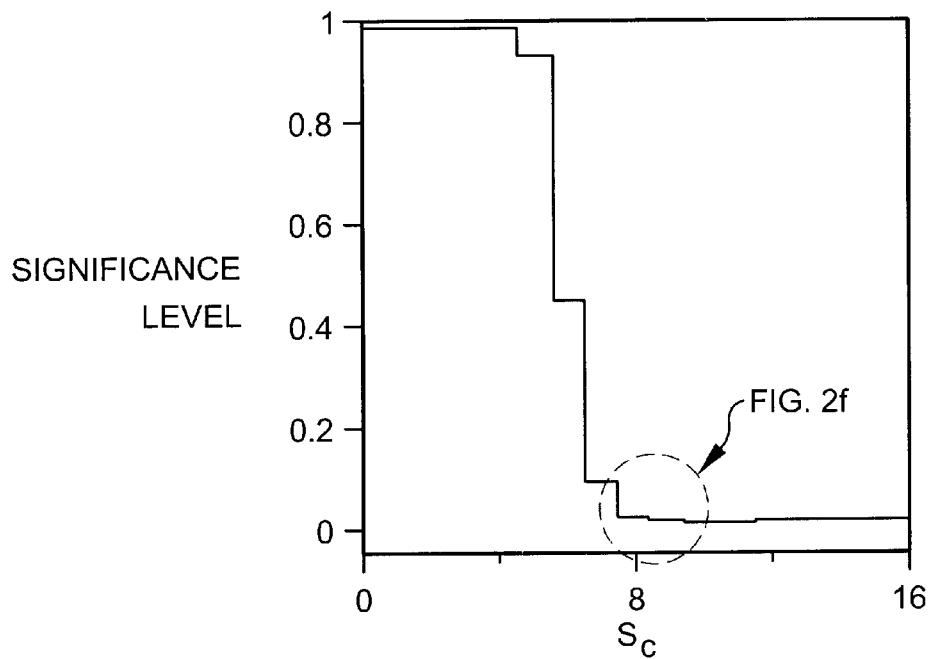
FIG. 2e: The significance level of FIG. 2d is shown as $\alpha$ function of $S_C$.
Figure 2F:
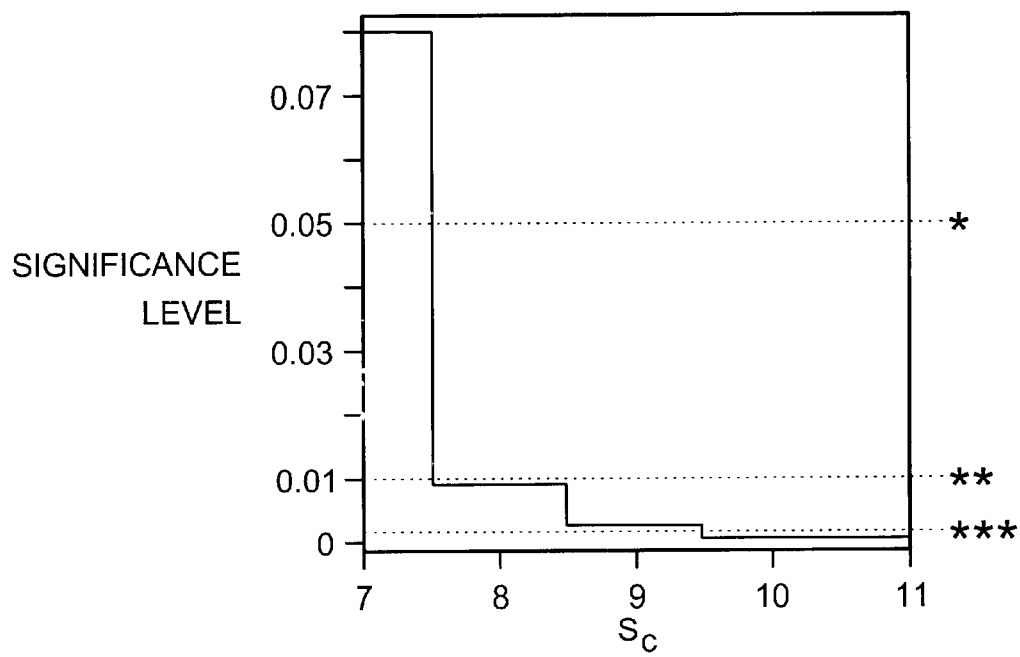
FIG. 2f: Magnified portion of FIG. 2e with horizontal lines indicating the significance levels: 0.05 (*), 0.01 () and 0.001 (*).

The simulated frequency distributions of the protein identification score for a set of random tryptic peptide maps of size 20 and 80 respectively are shown in FIG. 1. Apparently the fraction of the map that matches a database protein by chance drops as the map size increases (FIG. 1b). Knowledge of score frequency distributions of the type shown in FIG. 1 is the basis for testing the significance of protein identifications.

In the simplest form of significance testing, a null hypothesis $H_0$ is either rejected or not rejected at some significance level $\alpha$. Here, $H_0$ is defined as: "a protein-identification is random and false." In order to test the significance of an experimental result, the frequency function $f(S)$ describing $H_0$ must be known or estimated. By simulating many protein identifications using random tryptic peptide maps and by storing each identification score S while distinguishing between random and true (rare events) and random and false results, $f(S)$ could be estimated simply by dividing a score frequency distribution of the type shown in FIG. 1 by the number of simulated protein identifications (i.e. peptide maps). The problem of testing if a protein identification result deviates significantly from $H_0$ falls naturally into the category of one-sided significance testing using the protein identification score resulting from the experiment as the test variable. That is, if the score S is larger than a critical value $S_C$, $H_0$ is rejected, otherwise it is not rejected. $S_C$ is derived from the equation:

$$\sum_{S \geq S_C} f(S) \leq \alpha$$

(for a discrete distribution), where $\alpha$ is a significance level (sometimes called test error risk) chosen prior to the significance testing. $\alpha$ represents the statistical risk (probability) that $H_0$ would be rejected if it actually were true. Apparently $\alpha$ should be small, and often the values 0.05, 0.01, or 0.001 are chosen. FIG. 2 illustrates the entire procedure of employing simulated score distributions to estimate frequency functions and to find what scores correspond to a particular significance level.

The Number of Masses in the Peptide Map

Figure 3A:
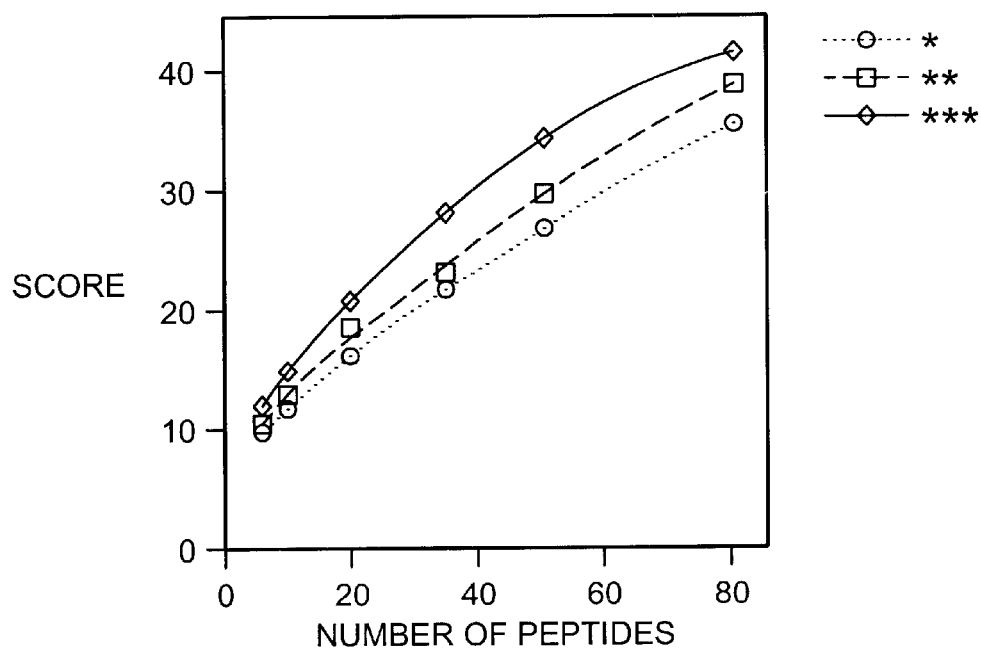
FIG. 3a: The scores corresponding to three different significance levels α=0.05 (*), 0.01 (**) and 0.001 (* * *) as a function of the number of tryptic peptide masses in a peptide map. The scores were generated using Algorithm 1. The lines through the simulated data points represent least square fits to second order polynomial functions.
Figure 3B:
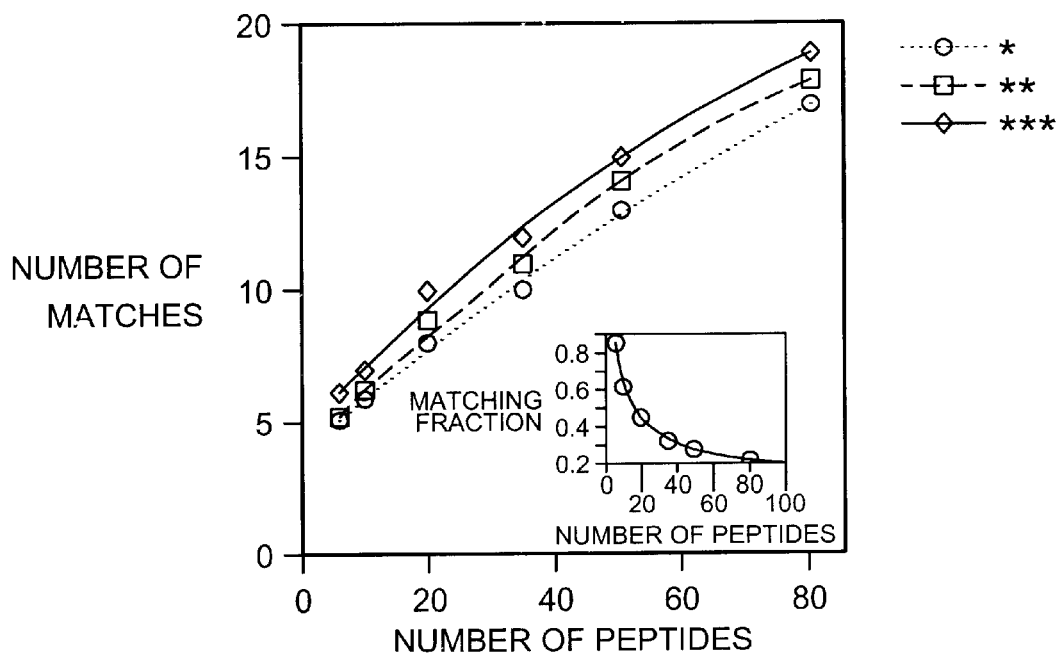
FIG. 3b: The scores corresponding to three different significance levels α=0.05 (*), 0.01 () and 0.001 (*) as a function of the number of tryptic peptide masses in a peptide map. The scores were generated using Algorithm 2. The lines through the simulated data points represent least square fits to second order polynomial functions. In the inset, scores (number of matches) corresponding to α=0.01 are shown relative to the number of peptides in the maps.
Figure 4A:
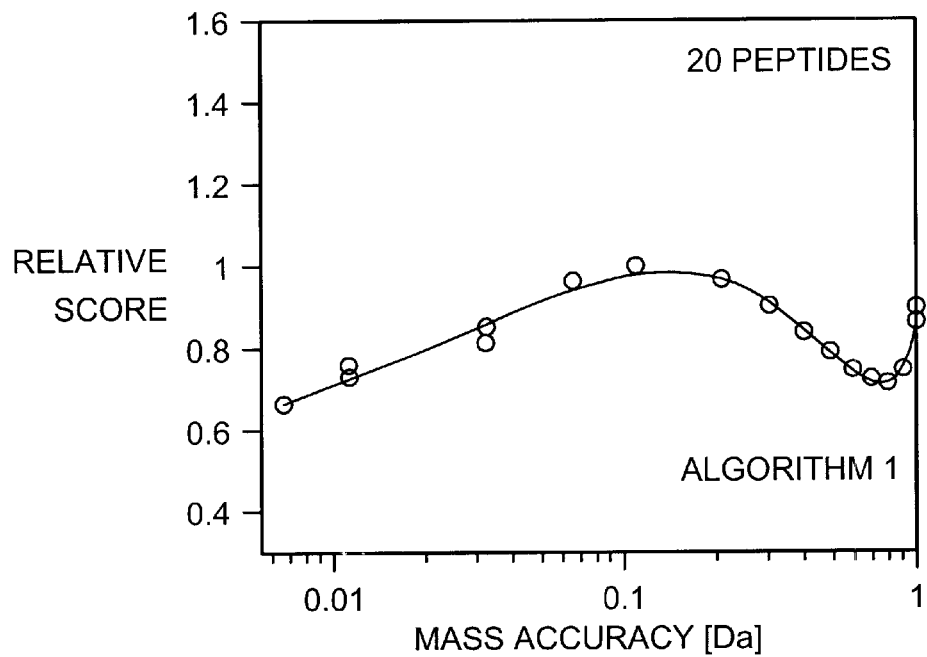
FIG. 4a: The score $S_C$ corresponding to α=0.01 as a function of the mass accuracy for random tryptic peptide maps with 20 masses. The scores were generated using Algorithm 1. The score $S_C$ was normalized to the value of $S_C$ for a mass accuracy of 0.1 Da.
Figure 4B:
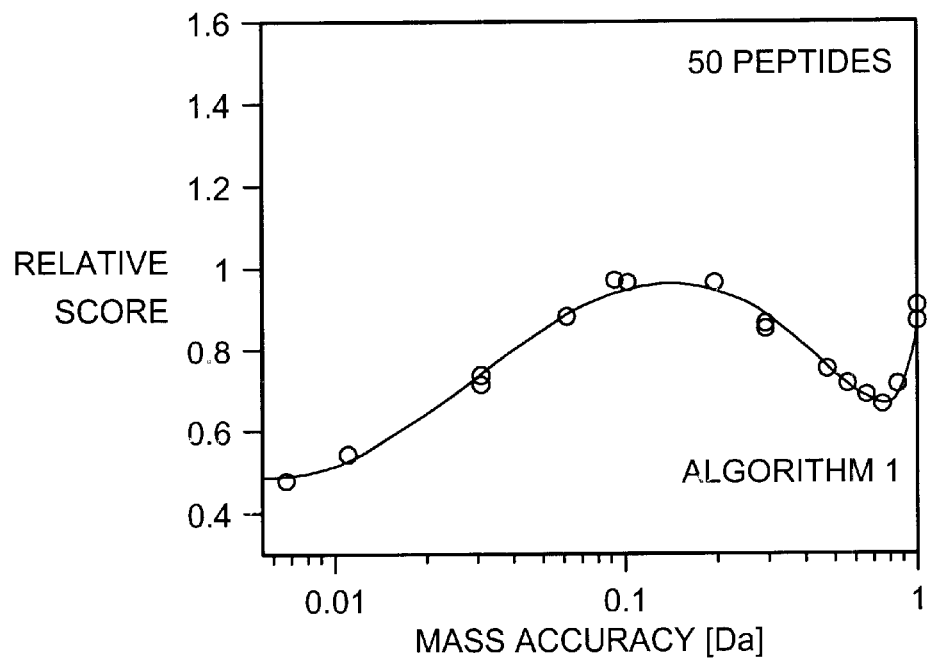
FIG. 4b: The score $S_C$ corresponding to α=0.01 as a function of the mass accuracy for random tryptic peptide maps with 50 masses. The scores were generated using Algorithm 1. Score $S_C$ was normalized to the value of $S_C$ for a mass accuracy of 0.1 Da.
Figure 4C:
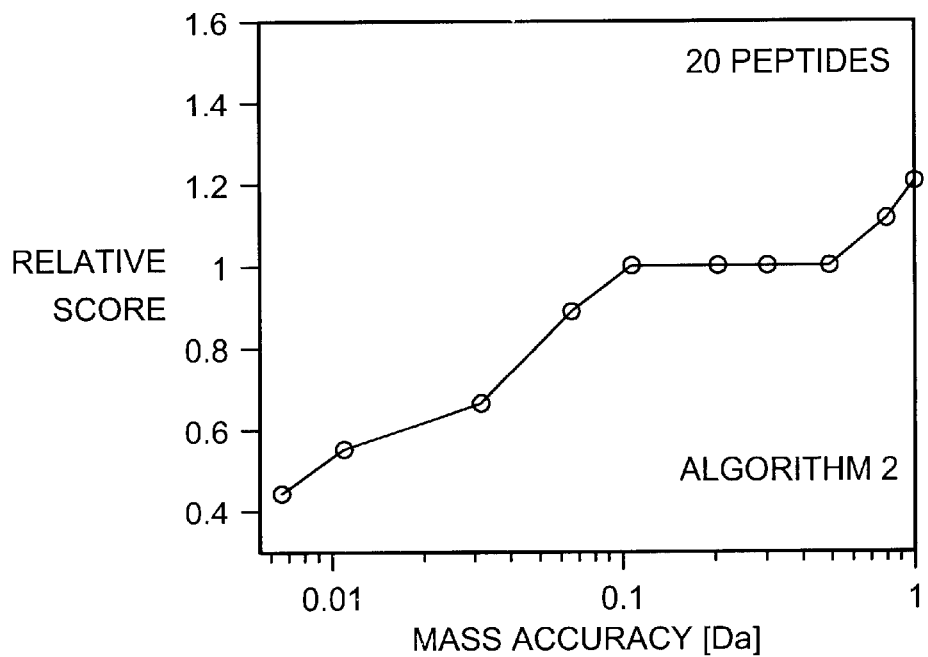
FIG. 4c: The score $S_C$ corresponding to α=0.01 as a function of the mass accuracy for random tryptic peptide maps with 20 masses. The scores were generated using Algorithm 2. Score $S_C$ was normalized to the value of $S_C$ for a mass accuracy of 0.1 Da.
Figure 4D:
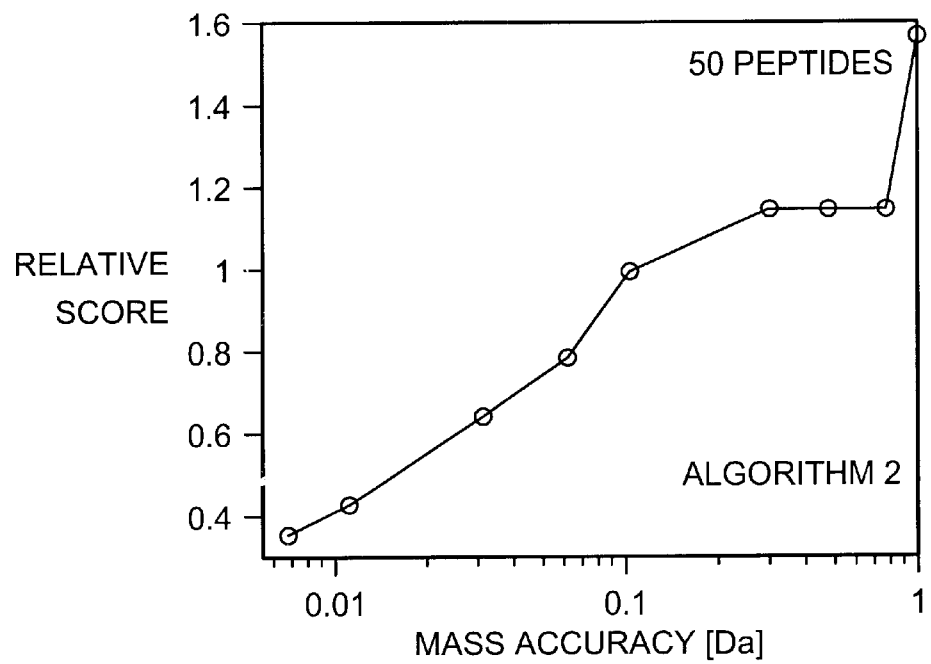
FIG. 4d: The score $S_C$ corresponding to α=0.01 as a function of the mass accuracy for random tryptic peptide maps with 50 masses. The scores were generated using Algorithm 2. Score $S_C$ was normalized to the value of $S_C$ for a mass accuracy of 0.1 Da.

In order to make significance testing applicable; one has to find the score $S_C$ required for a significance level $\alpha$ under the particular conditions of an experiment. For example, the number of tryptic peptide mass peaks can vary considerably between different experiments. The influence of the number of peaks on the score required for significant identification is illustrated in FIG. 3. It is seen clearly that a large peptide map is desirable in order to discriminate against false identifications.

Mass Accuracy

The mass accuracy $\Delta m$ in an experiment is typically entered in the database search. The entry should reflect the true $\Delta m$. State of the art instruments typically employed for peptide mapping can provide $\Delta m \leq 0.1$ Da for peptides. Here $\Delta m$ was varied between 0.006 and 1 Da. It is seen from FIG. 4, where $S_C$ is plotted versus $\Delta m$, that a further improvement of $\Delta m$ from the presently typical level with for example one order of magnitude would clearly facilitate unambiguous protein identifications. The local minima of the functions fitted to the data simulated with algorithm 1 (FIGS. 4a–b), are due to the non-uniform distribution of peptide masses in the database and that the score is proportional to $(\Delta m)^{-r}$, where r is the number of matches. Algorithm 2 yields a plateau due to the non-uniform distribution of peptide masses (FIG. 4, e–d).

Incomplete Enzymatic Cleavage

Figure 5A:
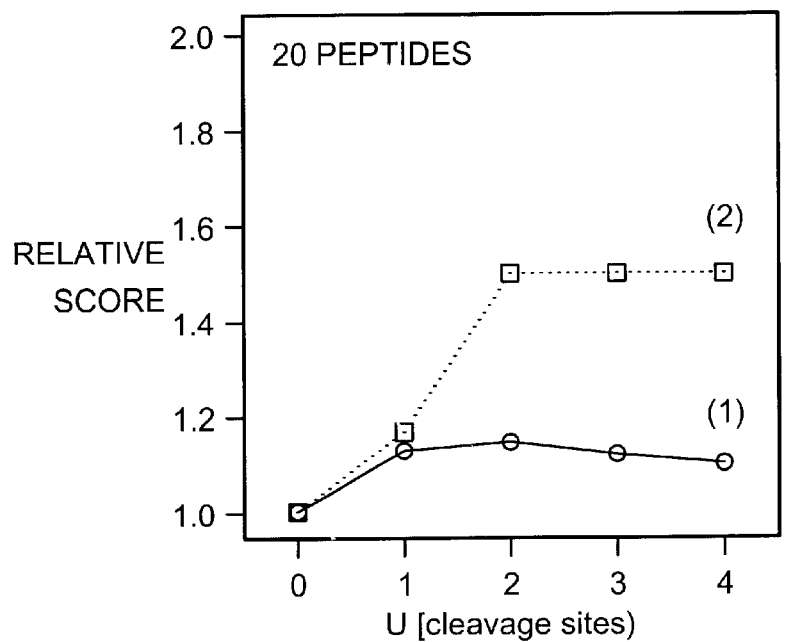
FIG. 5a: The protein identification score $S_C$ required for 1% significance (α=0.01) versus u, the maximum number of uncleaved cleavage sites allowed in the database search for Algorithm 1 (1) and Algorithm 2 (2). The results were normalized to the respective values of $S_C$ for u=0. Random tryptic peptide maps with 20 masses were used.

Enzymatic digestion is often imperfect. The expected highest number u of specific sites not cleaved in an experiment is typically entered as a constraint in the database search. Here, u was varied between 0 and 4 in different database searches. It is seen from the results in FIG. 5, where $S_C$ is plotted as a function of u, that an as complete cleavage as possible reduces the number of possibilities for random matching of peptide masses and therefore facilitates the discrimination against false results.

Figure 5B:
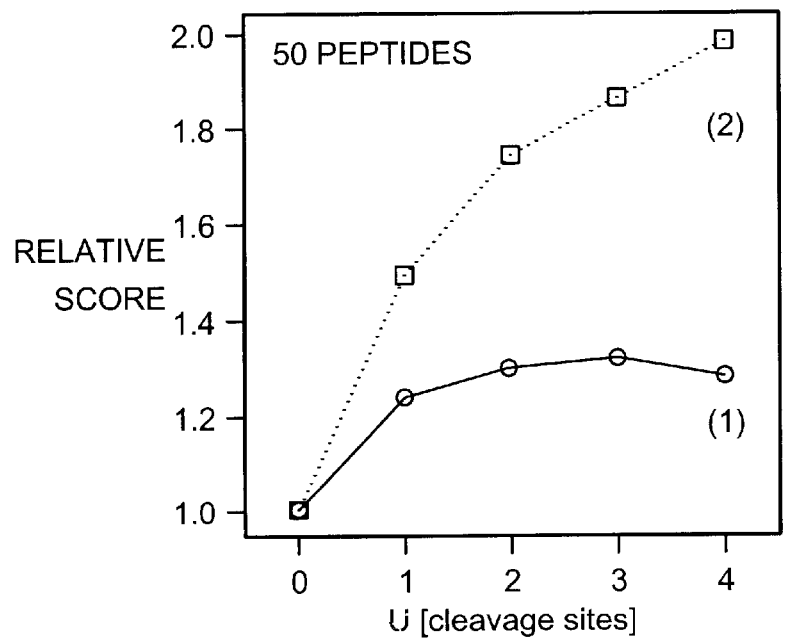
FIG. 5b: The protein identification score $S_C$ required for 1% significance (α=0.01) versus u, the maximum number of uncleaved cleavage sites allowed in the database search for Algorithm 1 (1) and Algorithm 2 (2). The results were normalized to the respective values of $S_C$ for u=0. Random tryptic peptide maps with 50 masses were used.

Algorithm 1 has an intrinsic moderation of the influence on the score S by the number N of possible proteolytic peptide masses per database protein: S is proportional to (N-r)!/N!, where r is the number of matches. This moderation causes a drop of $S_C$ for large values of u, as the number of matches either saturates (FIG. 5a) or begins to increase less steeply with u (FIG. 5b).

Independently of algorithm, the trend of saturation shown in FIG. 5 illustrates is that poor cleavage does not necessarily ruin an experiment, and incomplete cleavage can in fact sometimes yield further information. This extra information is not utilized in any of the scoring algorithms applied here.

Protein Mass

Figure 6A:
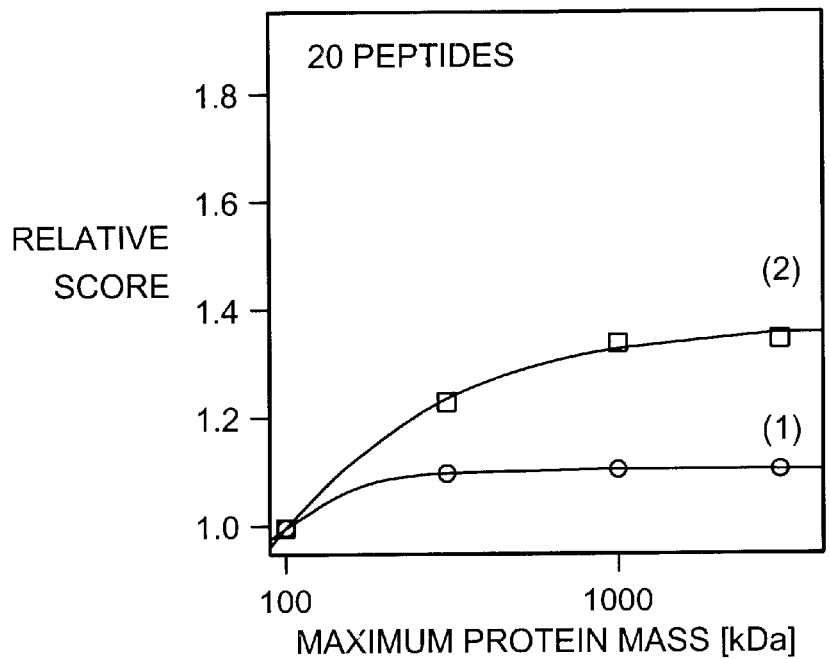
FIG. 6a: The score $S_C$ that yields α=0.01 as a function of the maximum protein mass allowed in the database search for Algorithm 1 (1) and Algorithm 2 (2). The results are shown relative to the respective $S_C$ obtained with a maximum protein mass of 100 kDa. Random tryptic peptide maps with 20 masses were used.
Figure 6B:
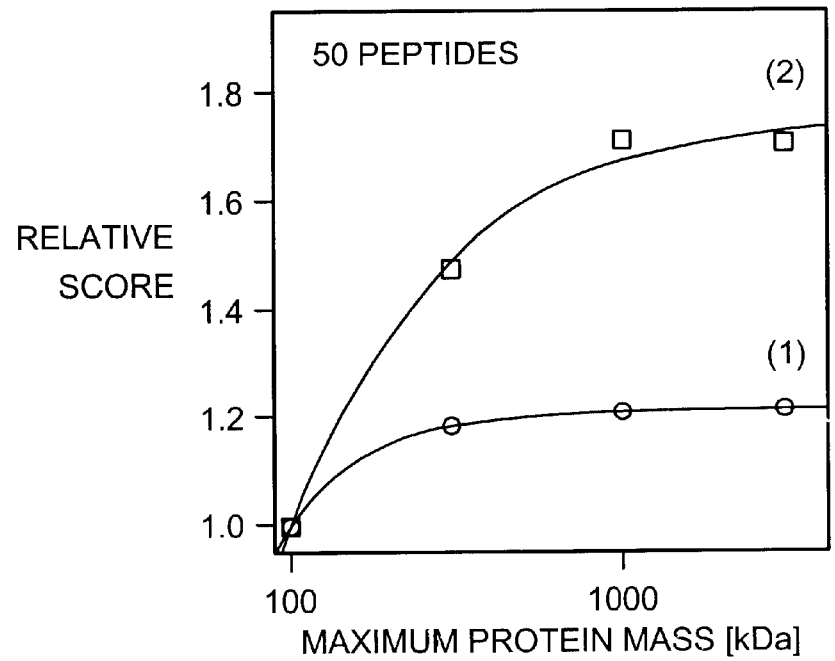
FIG. 6b: The score $S_C$ that yields α=0.01 as a function of the maximum protein mass allowed in the database search for Algorithm 1 (1) and Algorithm 2 (2). The results are shown relative to the respective $S_C$ obtained with a maximum protein mass of 100 kDa. Random tryptic peptide maps with 50 masses were used.

Due to potentially occurring protein degradation and anomalous migration of modified proteins in SDS-gel electrophoresis, mass information from gels as a constraint for protein identification should be used with caution. In most of the simulations, the protein mass was restricted to 100 kDa for the proteins generating the peptide maps as well as in the database search. About 95% of *S. cerevisiae* proteins are within this mass range. In order to cover the remaining 5% of proteins, the influence on the score required for significance as a function of the protein mass range was studied. FIG. 6 shows that algorithm 1 is rather insensitive to an increased protein mass range, whereas algorithm 2 yields a high degree of random matching with high-mass proteins.

Genome Size

Figure 7A:
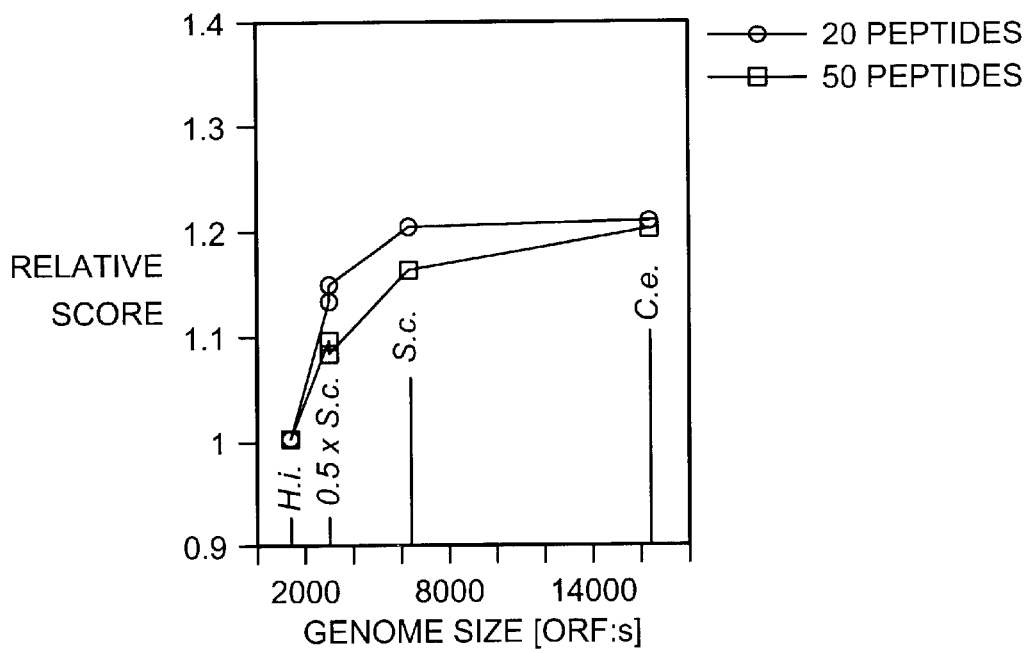
FIG. 7a: The influence of the size of the genome database on the protein identification score $S_C$ required for 1% significance. The simulated data represent *H. influenzae* (h.i.), *S. cerevisiae* (yeast) and *C. elegans* (c.e.). The yeast genome was divided into two parts of similar size and the results from the respective parts were averaged ($y_{1/2}$). The scores were generated using Algorithm 1.
Figure 7B:
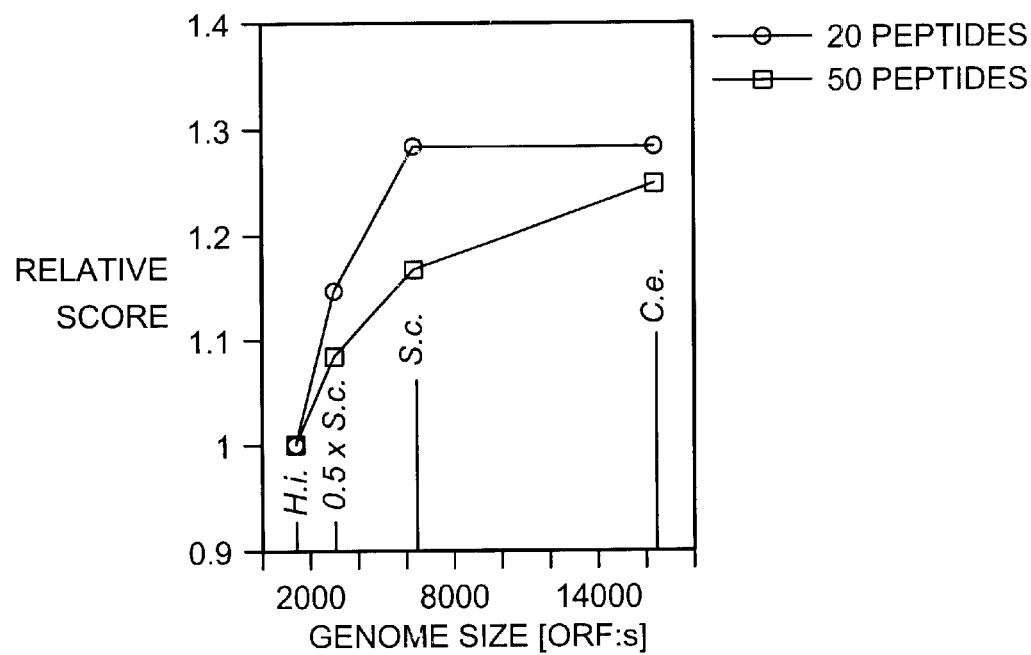
FIG. 7b: The influence of the size of the genome database on the protein identification score $S_C$ required for 1% significance. The simulated data represent *H. influenzae* (h.i.), *S. cerevisiae* (yeast) and *C. elegans* (c.e.). The yeast genome was divided into two parts of similar size and the results from the respective parts were averaged ($y_{1/2}$). The scores were generated using Algorithm 2.

The score required for significance, $S_C$, was studied as a function of the size of the genome. The results shown in FIG. 7 are based on data (random tryptic peptide maps) from a prokaryote *H. influenzae*, a single-cell eukaryote *S. cerevisiae* (budding yeast), and a multicellular organism *C. elegans* (nematode) respectively. The yeast genome was divided into two parts of similar size and the results from the respective parts were averaged. The score required for significant protein identification increases with the size of the genome (FIG. 7). Identification of *H. influenzae* and *C. elegans* proteins from random tryptic peptide maps generated from the *S. cerevisiae* genome yielded similar results as those of FIG. 7 (data not shown). This is due to the highly similar distribution of tryptic peptide masses for different genomes. Therefore, the dependence of $S_C$ on the genome size shown here can be used to estimate $S_C$ for any genome within the size range studied.

Statistical Uncertainties

The number of protein identifications simulated and the shape of the score frequency function can influence the accuracy of $S_C$, the score required for a significant result. How sensitive the value of $S_C$ is to statistical fluctuations was probed carefully by (1) repeated simulation with each simulation performed under identical conditions except for the set of random numbers used to generate the maps, and (2) by varying the number of random peptide maps used per simulation. The pronounced discrete nature of the score distribution of algorithm 2 implies an inherent sensitivity to statistical fluctuations in the simulations. When using algorithm 2 and maps composed of <35 peptides, the values of $S_C$ for $\alpha=0.01$ and $\alpha=0.001$ did not converge (jumped e.g. between 8 and 9 matches) as the number of peptide maps per simulation was increased ($\leq 15000$). For these significance levels and algorithm 2, the highest $S_C$ observed was assumed as the result. For larger peptide maps this potential uncertainty is reduced due to a broadening of the score frequency distribution (FIG. 1b). Significance testing with heavily discrete distributions can also cause a fairly large discrepancy between the values of $\alpha$ and P, where P is the area under the score frequency function $f(S)$ for $S \geq S_C$ (FIG. 2). For example, in the results for $\alpha=0.05$ plotted in FIG. 3 the median of the relative deviation $(\alpha-P)/\alpha$ was 0.63 for algorithm 2, but only 0.12 for algorithm 1.

The less discrete nature of algorithm 1 allows even minor statistical fluctuations to be resolved and examined. As several simulations with peptide maps generated by different random numbers were performed under identical conditions, the fluctuation of $S_C$ due to a different response to different random data could be probed. The standard deviation of the mean $S_C$ derived from five different simulations decreased sharply when going from 500 to 1000 maps per simulation and then changed very moderately when the number of maps was increased further. For five simulations each using 1000 maps with 20 random tryptic peptide masses, the relative standard deviation from the mean $S_C$ was 0.6%, 1.5%, and 2.5% for the 0.05, 0.01, and 0.001 significance levels respectively. The mean $S_C$ determined with 1000 maps per simulation differed by 0.4% from the $S_C$ determined by simulating with 15,000 maps. Hence, for algorithm 1 the magnitude of $S_C$ is well established already at 1000 maps per simulation, but statistical fluctuations between different data sets can in an individual simulation cause an uncertainty of a few percent.

To avoid potential bias by statistical fluctuations between different sets of random peptide maps (different simulations), the same set of random peptide maps was used when the respective functions of mass accuracy, the number of uncleaved sites, and maximum protein mass were derived (FIGS. 4–6). For the function describing the dependence on the maximum number of uncleaved sites (FIG. 5), the concept of using the same data-set was utilized by using random maps with completely cleaved peptides while varying the maximum number of uncleaved sites u in the database search. However, the relation between the relative score and u was the same as that plotted in FIG. 5 if instead the same u was used for the tryptic peptides in the random maps as in the database search (data not shown). For the function describing the dependence on the maximum protein mass (FIG. 6), random peptide maps generated with no limitation on the mass of the proteins contributing to the maps were used, and the protein mass range was varied in the database search only. A comparison was made between the results plotted in FIG. 6 (case 1) and results from simulations using the same protein mass limitations in the peptide maps as in the database search (case 2). For random maps with 20 tryptic peptides no difference was observed between case 1 and case 2. For simulations with 50 peptides in the random tryptic peptide maps, algorithm 1 displayed no clear difference between the two cases, whereas algorithm 2 yielded a slightly less pronounced dependence on the protein mass for case 2. The latter observation is due to that the random and true results, which occur at a frequency increasing with the number of peptides in the maps, are somewhat suppressed when the limitation of the protein mass is in the database search only. For example, if a protein with mass 400 kDa contributes with a peptide to a map, that protein can never be identified by chance when the database search is done with a protein mass limit of 300 kDa.

The approach of fitting score frequency functions to appropriate analytical functions could be a means of reducing difficulties associated with discrete distributions and statistical fluctuations. Such an approach remains to be explored for simulation of random protein identification, but has been employed for determination of scores required for significance in sequence or structure comparison algorithms.

Exploring a Large Parameter Space

The results presented in FIGS. 1–7 are based on 110 simulations including the two different scoring methods ($>10^5$ protein identifications). Clearly, these simulations represent a small fraction even of the limited range of various search parameters studied. To generate a mesh within which interpolation could be accurately performed would require about $10^7$ protein identifications per algorithm. This is quite feasible and would require about 30 days of computation time per algorithm on a regular PC. A less computationally intensive approach is to/use the functions that describe how $S_C$ varies in the parameter space studied (FIGS. 3–7). We tested this approach by comparing such estimations of $S_C$ with values of $S_C$ derived from direct simulations for randomly chosen points in the parameter space. A very good correlation between estimation and simulation was obtained (0–5% deviation, similar to the uncertainty in $S_C$ from a single simulation). Therefore, estimation based on the functions derived here is an accurate procedure to assess $S_C$ in an arbitrary point in the parameter space.

The Design of Tryptic Peptide Maps

The hypothetical data used in the protein identification simulations were random tryptic peptide maps. These maps were used with the specific goal to elucidate the distribution of scores due to random matching between the masses of the hypothetical tryptic peptide map and theoretical masses of tryptic peptides of proteins in the database. The random matching can be studied in various ways. Completely random peptide maps, where each proteolytic peptide mass is generated from a different protein, and hence are non-correlated, is the most straightforward alternative. The random peptide maps represent an extreme protein mixture (or one or more heavily modified proteins), that might be unrealistic. The null hypothesis $H_0$: the protein identification is false and random, could be investigated by data that are closer to what a researcher would expect to observe experimentally. But, the significance testing of the deviation from $H_0$ does not suggest that real data would often strongly resemble the score distribution for random matching. The interesting part of the random score distribution is the high-score-side where the score distribution of real data could presumably overlap, hence making the real and the random distributions indistinguishable. If simulation with data from 6 proteins in a map with 20 tryptic peptides is done, and all possible combinations of the number of peptides per protein in the map are used with equal abundance, the number of true results increases compared with the completely random maps, and the true results typically yield higher scores. Apparently, true and false results can also yield similar scores. As expected, the scores of the false results are similar if the map is constructed from 6 or from 20 proteins. However, the small number of false results yielded with 6 proteins provide poor statistics for the score distribution necessary to describe $H_0$, and hence the estimate of the score corresponding to significance would become considerably more uncertain.

TABLE 1

Simulation Parameters

| Genome | S. CEREVISIAE |
|---|---|
| Number of tryptic peptides in a map | N |
| Number of uncleaved sites in map peptides | 0 |
| Number of proteins contributing to a map | N |
| Number of maps used in a sumilation | 1000 |
| Maximum number of uncleaved sites allowed in the database search | 2 |
| Mass accuracy in the database search [Da] | 0.1 |
| Maximum protein mass in data generation and database searches [kDa] | 100 |

The protein identification simulation conditions employed unless otherwise stated.

TABLE 2

Result from a ProFound Search of All *S. Cerevisiae* Proteins in OWL with Masses from FIG. 3a 1. IF42__YEAST (probability = 7.9c-01) EUKARYOTIC INITIATION FACTOR 4F SUBUNIT P130
2. NPR1__YEAST (probability = 2.8e-02) NITROGEN PERMEASE REACTIVATOR PROTEIN
3. S63138 (probability = 1.9e-02) PROBABLE PROTEIN KINASE NPR1
4. RL3E__YEAST (probability = 1.8c-02) 60S RIBOSOMAL PROTEIN L30E
5. SCYOR206W (probability = 1.5e-02) HYPOTHETICAL PROTEIN SCYOR206W
6. CBF5__YEAST (probability = 1.4c-02) CENTROMERE/ MICROTUBULE BINDING PROTEIN CBF5
7. S52893 (probability = 9.5e-03) HYPOTHETICAL PROTEIN YMR044W Note:
m/z = 2164 and 2275 were not used in the search, because they are from autolysis of trypsin.

TABLE 3

CGI Programs Currently Used for Protein Identification

| CGI program | Data type | Databases | Cleavage chemistry | Additional search parameters | Help | AI | Report format |
|---|---|---|---|---|---|---|---|
| PepFrag [21] | MS/MS | 10 (aa + na) | 7 Enzymes + CNBr | Protein mass, peptide masses, taxonomy, missed cleavage sites, daughter ion types, mass accuracy | Pages + examples | No | Active + tools |

TABLE 3-continued

CGI Programs Currently Used for Protein Identification

| CGI program | Data type | Databases | Cleavage chemistry | Additional search parameters | Help | AI | Report format |
|---|---|---|---|---|---|---|---|
| ProFound [22] | Masses | 1 (aa) | 5 Enzymes + CNBr | Protein mass, taxonomy, missed cleavage sites, mass accuracy | Pages + examples | Yes | Active + tools |
| MS-Fit [23] | Masses | 5 (aa + na) | 9 Enzymes + CNBr | Protein mass, taxonomy, missed cleavage sites, mass accuracy | 1 Example | No | Active |
| MS-Tag [24] | MS/MS | 5 (aa + na) | 9 Enzymes + CNBr | Protein mass, taxonomy, missed cleavage sites, daughter ion types, mass accuracy | 1 Page | No | Active |
| PeptideSearch [25] | Masses | 1 (na) | 7 Enzymes + CNBr | Protein mass, mass accuracy | None | No | Active |
| PeptideSearch [26] | MS/MS | 1 (na) | 7 Enzymes + CNBr | Protein mass, daughter ion types, mass accuracy | None | No | Active |
| Mass Search [27] | Masses | 2 (aa + na) | 11 Enzymes + 7 chemical | Protein mass | 1 example | No | Dead |
| Mowse [28] | Masses | 1 (aa) | 6 Enzymes + CNBr | Protein mass, amino acid composition, mass accuracy | 1 Page | Yes | Active |

Note:
Abbreviations: aa, amino acid sequence database; na, nucleic acid sequence database; CNBr, cyanogen bromide; and AI, any type of artificial intelligence/expert system used to rate results. An "active" report format has links that you can follow to get the sequence of a matched protein, and "tools" refer to additional programs to help make use of that sequence information. A "dead" report just lists the matching proteins' names and the user is expected to find the sequence information and pass judgment on the results without any assistance.

TABLE 4

Sequence Databases Currently Used for Protein Bioinformatics

| Database | Peptide sequences | Nucleic acid sequences | Peptide annotation | Redundancy | Sequence reliability | Entries (/1000) |
|---|---|---|---|---|---|---|
| SWISSPROT [3] | Yes | No | Complete | Low | Excellent | 50 |
| PIR [4] | Yes | No | Complete | Moderate | Excellent | 95 |
| EMBL [5] | No | Yes | Some | High | Good | 1438 |
| TREMBL [5] | Yes | No | Some | High | Good | 137 |
| GENBANK [6] | No | Yes | Some | High | Good | 1766 |
| GENPEPT [6] | Yes | No | Some | High | Good | 262 |
| OWL [7] | Yes | No | Some | Low | Good | 210 |
| dbEST [8] | No | Yes | None | Very high | Low | 1317 |

Note:
The sequence reliability for GENBANK and EMBL refers to the normal nucleic acid sequences stored in those databases. These databases also include expressed sequence tag data, which are not as reliable.

We claim:

1. A method of generating a frequency distribution of scores for a particular experimental condition, wherein the scores relate to random identifications of biological molecules, the method comprising:
   a) generating mass data for the particular experimental condition for biological molecules in a biological molecule database, wherein each biological molecule comprises a set of constituent parts;
   b) generating mass data of a hypothetical biological molecule for the experimental condition, wherein the hypothetical biological molecule comprises a set of constituent parts, and wherein the set of constituent parts of the hypothetical biological molecule is different from every set of constituent parts of each biological molecule of the database;
   c) comparing the data generated in step (b) with the data generated for each biological molecule in step (a);
   d) calculating a score for each comparison in step (c), wherein the score is a function of similarity between the data generated in step (a), which corresponds to a particular database biological molecule, and the data generated in step (b);
   e) selecting a score from the top twenty scores calculated in step (d), wherein the top twenty scores denote a high degree of similarity;
   f) repeating steps (b) through (e) with different hypothetical biological molecules until a sufficient quantity of scores are selected; and
   g) determining the frequency of selecting each score and generating therefrom a frequency distribution of scores.

2. A method of identifying an experimental biological molecule for a particular experimental condition and a particular significance level, wherein the statistical significance of the identification is assessed, the method comprising:
   a) selecting a significance level that represents a level of confidence in a biological molecule identification;
   b) cleaving the experimental biological molecule into constituent parts;

c) generating mass data for these constituent parts;

d) comparing the mass data generated in step (c) with mass data generated for the experimental condition from biological molecules of a biological molecule database;

e) calculating scores for each comparison in step (d), wherein the scores are a function of similarity between mass data of the experimental biological molecule and mass data generated from the biological molecule database;

f) selecting a score generated in step (e) wherein the score corresponds to a comparison which denotes a high degree of similarity and wherein the score corresponds to a particular biological molecule in the biological molecule database;

g) comparing the score selected in step (f) with a frequency distribution of scores for the experimental condition, wherein the frequency distribution relates to random biological molecule identifications, wherein the frequency distribution has associated therewith a critical score which corresponds to the significance level, and wherein the distribution is generated by:
   i) generating mass data of a hypothetical biological molecule, wherein the hypothetical biological molecule comprises a set of constituent parts, and wherein the set of constituent parts of the hypothetical biological molecule is different from every set of constituent parts of each biological molecule of the database;
   ii) comparing mass data of the hypothetical biological molecule with mass data of biological molecules in the database;
   iii) calculating a score for each comparison, wherein the score is a function of similarity between the mass data of the hypothetical biological molecule and the mass data of the biological molecules in the database;
   iv) selecting a score from the top twenty scores, wherein the top twenty scores denote a high degree of similarity;
   v) repeating steps (i) to (iv) with different hypothetical biological molecules until a sufficient quantity of scores are selected; and determining the frequency of selecting each score and generating therefrom the frequency distribution of scores relating to random identifications; and h) determining whether the score selected in step (f) is equal to or larger than the critical score, wherein if the score selected in step (f) is equal to or larger than the critical score, the identification of the experimental biological molecule is statistically significant for the selected significance level.

3. A method of determining statistical significance of a biological molecule identification score, the method comprising:

a) selecting a significance level that represents a level of confidence in a biological molecule identification;

b) calculating a score associated with an experimental biological molecule, wherein the score is a function of similarity between mass data of the experimental biological molecule and mass data generated for biological molecules of a biological molecule database;

c) comparing the score with a score frequency distribution, wherein the distribution relates to random biological molecule identifications, wherein the frequency distribution has associated therewith a critical score which corresponds to the significance level, and wherein the distribution is generated by:
   i) generating mass data of a hypothetical biological molecule, wherein the hypothetical biological molecule comprises a set of constituent parts, and wherein the set of constituent parts of the hypothetical biological molecule is different from every set of constituent parts of each biological molecule of the database;
   ii) comparing mass data of the hypothetical biological molecule with mass data of biological molecules in the database;
   iii) calculating a score for each comparison, wherein the score is a function of similarity between the mass data of the hypothetical biological molecule and the mass data of the biological molecules in the database;
   iv) selecting a score from the top twenty scores, wherein the top twenty scores denote a high degree of similarity;
   v) repeating steps (i) to (iv) with different hypothetical biological molecules until a sufficient quantity of scores are selected; and determining the frequency of selecting each score and generating therefrom the frequency distribution of scores relating to random identifications; and d) determining whether the score associated with the experimental biological molecule identification is equal to or larger than the critical score corresponding with the significance level, wherein if the score is equal to or larger than the critical score, the identification of the experimental biological molecule is statistically significant for the selected significance level.

4. A means for generating a frequency distribution of scores for a particular experimental condition, wherein the scores relate to random identifications of biological molecules, comprising:

a) a means for generating mass data for the particular experimental condition for biological molecules in a biological molecule database;

b) a means for generating mass data of a hypothetical biological molecule for the experimental condition, wherein the hypothetical biological molecule comprises a set of constituent parts, and wherein the set of constituent parts of the hypothetical biological molecule is different from every set of constituent parts of each biological molecule of the database;

c) a means for comparing the data generated in step (b) with the data generated for each biological molecule in step (a);

d) a means for calculating a score for each comparison in step (c), wherein the score is a function of similarity between the data generated in step (a) which corresponds to a particular biological molecule and the data generated in step (b);

e) a means for selecting a score from the top twenty scores calculated in step (d), wherein the selected score corresponds to the comparison which denotes a high degree of similarity between the data generated in step (a) and the data generated in step (b);

f) a means for repeating steps (b) through (e) with different hypothetical biological molecules until a sufficient quantity of scores are selected; and g) a means for determining the frequency of selecting each score and generating therefrom a frequency distribution of scores.

5. A means for identifying an experimental biological molecule for a particular experimental condition and a particular significance level comprising:
   a) a means for selecting a significance level that represents a level of confidence in a biological molecule identification;
   b) a means for cleaving the experimental biological molecule into constituent parts by a method that produces constituent parts;
   c) a means for generating mass data for these constituent parts;
   d) a means for comparing the mass data generated in step (c) with mass data generated for the experimental condition from biological molecules of a biological molecule database;
   e) a means for calculating scores for each comparison in step (d), wherein the scores are a function of similarity between mass data of the experimental biological molecule and mass data generated from the biological molecule database;
   f) a means for selecting a score generated in step (e) wherein the score corresponds to a comparison which denotes a high degree of similarity and wherein the score corresponds to a particular biological molecule in the biological molecule database;
   g) a means for comparing the score selected in step (f) with a frequency distribution of scores for the experimental condition, wherein the frequency distribution relates to random biological molecule identifications, wherein the frequency distribution has associated therewith a critical score which corresponds to the significance level, and wherein the distribution is generated by:
      i) generating mass data of a hypothetical biological molecule, wherein the hypothetical biological molecule comprises a set of constituent parts, and wherein the set of constituent parts of the hypothetical biological molecule is different from every set of constituent parts of each biological molecule of the database;
      ii) comparing mass data of the hypothetical biological molecule with mass data of biological molecules in the database;
      iii) calculating a score for each comparison, wherein the score is a function of similarity between the mass data of the hypothetical biological molecule and the mass data of the biological molecules in the database;
      iv) selecting a score from the top twenty scores, wherein the top twenty scores denote a high degree of similarity;
      v) repeating steps (i) to (iv) with different hypothetical biological molecules until a sufficient quantity of scores are selected; and determining the frequency of selecting each score and generating therefrom the frequency distribution of scores relating to random identifications; and
   h) a means for determining whether the score selected in step (f) is equal to or larger than the critical score, wherein if the score selected in step (f) is equal to or larger than the critical score, the identification of the experimental biological molecule is statistically significant for the selected significance level.

6. A means for determining statistical significance of a biological molecule identification score, comprising:
   a) a means for selecting a significance level that represents a level confidence in a biological molecule identification;
   b) a means for calculating a score associated with the experimental biological molecule, wherein the score is a function of similarity between mass data of the experimental biological molecule and mass data generated from a biological molecule database;
   c) a means for comparing the score with a score frequency distribution, wherein the distribution relates to random biological molecule identifications, wherein the frequency distribution has associated therewith a critical score which corresponds to the significance level, and wherein the distribution is generated by:
      i) generating mass data of a hypothetical biological molecule, wherein the hypothetical biological molecule comprises a set of constituent parts, and wherein the set of constituent parts of the hypothetical biological molecule is different from every set of constituent parts of each biological molecule of the database;
      ii) comparing mass data of the hypothetical biological molecule with mass data of biological molecules in the database;
      iii) calculating a score for each comparison, wherein the score is a function of similarity between the mass data of the hypothetical biological molecule and the mass data of the biological molecules in the database;
      iv) selecting a score from the top twenty scores, wherein the top twenty scores denote a high degree of similarity;
      v) repeating steps (i) to (iv) with different hypothetical biological molecules until a sufficient quantity of scores are selected; and determining the frequency of selecting each score and generating therefrom the frequency distribution of scores relating to random identifications; and
   d) a means for determining whether the score associated with the experimental biological molecule identification is equal to or larger than the critical score corresponding with the significance level, wherein if the score is equal to or larger than the critical score, the identification of the experimental biological molecule is statistically significant for the selected significance level.

7. A computer program product comprising:
a computer usable medium having computer readable program code means embodied in said medium for generating a frequency distribution of scores, wherein the scores relate to random identifications of biological molecules, said computer program product including:
   computer readable program code means for causing a computer to generate mass data for biological molecules in a biological molecule database for a particular experimental condition;
   computer readable program code means for causing the computer to generate mass data of a hypothetical biological molecule for the experimental condition, wherein the hypothetical biological molecule comprises a set of constituent parts, and wherein the set of constituent parts of the hypothetical biological molecule is different from every set of constituent parts of each biological molecule of the database;
   computer readable program code means for causing the computer to compare the mass data of the hypothetical biological molecule with the mass data generated for em biological molecules in the biological molecule database for the particular experimental condition;

computer readable program code means for causing the computer to calculate a score for each mass data comparison, wherein the score is a function of similarity between the mass data corresponding to a particular database biological molecule and the mass data corresponding to the hypothetical biological molecule;

computer readable program code means for causing the computer to select a score from the top twenty calculated scores, wherein the selected score corresponds to the comparison which denotes a high degree of similarity between the mass data corresponding to the particular database biological molecule and the mass data corresponding to the hypothetical biological molecule;

computer readable program code means for causing the computer to repeatedly generate mass data of different hypothetical biological molecules, compare the mass data of the hypothetical molecules with the mass data generated for biological molecules in the biological molecule database, calculate a score for each of the mass data comparisons and select a score from the calculated scores until a sufficient quantity of scores are selected; and computer readable program code means for causing the computer to determine the frequency of selecting each score and to generate therefrom a frequency distribution of scores.

8. A computer program product comprising:

a computer usable medium having computer readable program code means embodied in said medium for identifying an experimental biological molecule for a particular experimental condition and a particular significance level, said computer program product including:

computer readable program code means for causing a computer to generate mass data of an experimental biological molecule, the experimental biological molecule having been cleaved into constituent parts by a method that produces constituent parts;

computer readable program code means for causing the computer to compare the mass data of the experimental biological molecule with mass data generated for the experimental condition from biological molecules of a biological molecule database;

computer readable program code means for causing the computer to calculate scores for each mass data comparison, wherein the scores are a function of similarity between mass data of the experimental biological molecule and mass data generated from the biological molecule database;

computer readable program code means for causing the computer to select a score from the calculated scores, wherein the selected score corresponds to a particular biological molecule in the biological molecule database, and wherein the selected score corresponds to a comparison which denotes a high degree of similarity;

computer readable program code means for causing the computer to compare the selected score with a frequency distribution of scores for the experimental condition, wherein the distribution relates to random biological molecule identifications, wherein the frequency distribution has associated therewith a critical score which corresponds to the significance level, and wherein the distribution is generated by:

i) generating mass data of a hypothetical biological molecule, wherein the hypothetical biological molecule comprises a set of constituent parts, and wherein the set of constituent parts of the hypothetical biological molecule is different from every set of constituent parts of each biological molecule of the database;

ii) comparing mass data of the hypothetical biological molecule with mass data of biological molecules in the database;

iii) calculating a score for each comparison, wherein the score is a function of similarity between the mass data of the hypothetical biological molecule and the mass data of the biological molecules in the database;

iv) selecting a score from the top twenty scores, wherein the top twenty scores denote a high degree of similarity;

v) repeating steps (i) to (iv) with different hypothetical biological molecules until a sufficient quantity of scores are selected; and determining the frequency of selecting each score and generating therefrom the frequency distribution of scores relating to random identifications; and computer readable program code means for causing the computer to determine whether the selected score is equal to or larger than the critical score.

9. A computer program product comprising:

a computer usable medium having computer readable program code means embodied in said medium for determining statistical significance of a biological molecule identification score, said computer program product including:

computer readable program code means for selecting a significance level that represents a level confidence in a biological molecule identification, wherein the significance level has a corresponding critical score;

computer readable program code means for causing a computer to calculate a score associated with an experimental biological molecule, wherein the score is a function of similarity between mass data of the experimental biological molecule and mass data generated from a biological molecule database;

computer readable program code means for causing the computer to compare the score with a score frequency distribution, wherein the frequency distribution relates to random biological molecule identifications, wherein the frequency distribution has associated therewith a critical score which corresponds to the significance level, and wherein the distribution is generated by:

i) generating mass data of a hypothetical biological molecule, wherein the hypothetical biological molecule comprises a set of constituent parts, and wherein the set of constituent parts of the hypothetical biological molecule is different from every set of constituent parts of each biological molecule of the database;

ii) comparing mass data of the hypothetical biological molecule with mass data of biological molecules in the database;

iii) calculating a score for each comparison, wherein the score is a function of similarity between the mass data of the hypothetical biological molecule and the mass data of the biological molecules in the database;

iv) selecting a score from the top twenty scores, wherein the top twenty scores denote a high degree of similarity;

v) repeating steps (i) to (iv) with different hypothetical biological molecules until a sufficient quantity of scores are selected; and determining the frequency of selecting each score and generating therefrom the frequency distribution of scores relating to random identifications; and computer readable program code means for causing the computer to determine whether the score associated with the experimental biological molecule identification is equal to or larger than the critical score associated with the significance level, wherein if the score is equal to or larger than the critical score, the identification of the experimental biological molecule is statistically significant for the selected significance level.

10. The method according to claim 1 wherein a function is derived from the frequency distribution.

11. The method according to claim 10 wherein the function derived from the frequency distribution is a discrete function.

12. The method according to claim 10 wherein the function derived from the frequency distribution is a probability density function.

13. The method according to claim 1 wherein the mass data in step (a) are generated by a computer.

14. The method according to claim 1 wherein the mass data in step (b) are generated by a computer.

15. The method according to claim 1 wherein the mass data in step (b) are generated by a mass spectrometer analysis of an enzymatic digest of a complicated mixture of proteins.

16. The method of claim 1 wherein the database biological molecules and hypothetical biological molecules are proteins.

17. The method of claim 1 wherein the database biological molecules and hypothetical biological molecules are nucleic acid molecules.

18. The method of claim 1 wherein the database biological molecules and hypothetical biological molecules are polysaccharides.

19. The method according to claim 1 wherein a sufficient quantity of scores is in the range of from about 1 to $10^{10}$ scores.

20. The method according to claim 1 wherein a sufficient quantity of scores is in the range of from about 100 to $10^7$ scores.

21. The method according to claim 1 wherein the experimental condition defines the mass data as resulting from chemical or enzymatic degradation of the database biological molecules and hypothetical biological molecules.

22. The method according to claim 21 wherein the experimental condition defines an efficiency of the chemical or enzymatic degradation.

23. The method of claim 21 wherein the enzymatic digestion is by trypsin.

24. The method according to claim 1 wherein the comparison in step (c) is constrained to database biological molecules within a chosen mass range.

25. The method according to claim 1 wherein the biological molecule is a protein, and wherein the comparison in step (c) is constrained to database proteins within a chosen isoelectric point range.

26. The method according to claim 1 wherein the experimental condition defines a particular accuracy for mass data determination.

27. The method according to claim 1 wherein the comparison in step (c) comprises database biological molecules which exhibit modifications.

28. The method according to claim 27 wherein the modifications of the biological molecules are posttranslational modifications of proteins.

29. The method according to claim 1 wherein the hypothetical biological molecule is generated by a method which comprises:
a) selecting at least one biological molecule from a biological molecule database;
b) generating mass data of the biological molecule in step (a);
c) selecting a mass from step (b) which corresponds to at least one constituent part of the database biological molecule;
d) repeating steps (a) through (c) for a different selected biological molecule until a sufficient number of masses are selected to generate a hypothetical biological molecule.

30. The method according to claim 29 wherein the biological molecule in step (a) is randomly selected.

31. The method according to claim 29 wherein the constituent part of the biological molecule in step (c) is randomly selected.

32. The method according to claim 29 wherein the hypothetical biological molecule comprises a set of constituent parts which is different from every set of constituent parts of the database biological molecules of the biological molecule database.

33. The method of claim 29 wherein the constituent parts comprise peptides.

34. The method of claim 29 wherein the constituent parts comprise oligonucleotides.

35. The method of claim 29 wherein the constituent parts comprises polysaccharides.

36. The method according to claim 29 wherein a sufficient number of masses selected in step (c) is in the range of from about 1 to about 1000.

37. The method according to claim 29 wherein the biological molecule of step (a) is within a chosen mass range.

38. The method according to claim 37 wherein the chosen mass range is from about 0.1 to about 3000 kDa.

39. The method according to claim 1 wherein fragment mass data is generated for at least one constituent part of the database biological molecules and hypothetical biological molecule.

40. The method according to claim 39 wherein the comparison between data for each of the database biological molecules and the hypothetical biological molecule comprises the comparison of the fragment mass data.

41. The method according to claim 39 wherein the experimental condition defines the energy used to generate the fragment mass data.

42. The method according to claim 2 wherein the experimental biological molecule is cleaved into constituent parts by a method that produces constituent parts in a predictable way.

43. The method according to claim 2 wherein the mass data of step (c) are generated by a mass spectrometer.

44. The method according to claim 2 wherein the experimental biological molecule is in a mixture of biological molecules.

45. The method according to claim 2 wherein the comparison in step (d) is constrained to database biological molecules within a chosen mass range.

46. The method according to claim 45 wherein the chosen mass range is within 25% of the mass of the experimental biological molecule.

47. The method according to claim 45 wherein the chosen mass range within is from about 0.1 to about 3 000 kDa.

48. The method according to claim 2 wherein the experimental condition defines the mass data as resulting from chemical or enzymatic degradation of the database biological molecules and hypothetical biological molecules.

49. The method according to claim 48 wherein the experimental condition defines efficiency of the chemical or enzymatic degradation.

50. The method according to claim 2 wherein the biological molecule is a protein, and wherein the comparison in step (d) is constrained to proteins of the database which have an isoelectric point within a particular range.

51. The method according to claim 50 wherein the isoelectric point range is within 25% of the isoelectric point of the experimental biological molecule.

52. The method according to claim 2 wherein the experimental, condition defines a particular accuracy for the determination of the mass data.

53. The method according to claim 2 wherein the comparison in step (d) comprises database biological molecules which exhibit modifications.

54. The method according to claim 2 wherein fragment mass data is generated for at least one constituent part of the database biological molecules and hypothetical biological molecules.

55. The method according to claim 54 wherein the comparison between data for each of the database biological molecules and the hypothetical biological molecule comprises the comparison of the fragment mass data.

56. The method according to claim 54 wherein the experimental condition defines the energy used to generate the fragment mass data.

57. The method according to claim 56 wherein the fragment mass data is generated by vibrational excitation.

58. The method according to claim 56 wherein the fragment mass data is generated by electronic excitation.

59. The method according to claim 51 wherein the vibrational excitation is generated by collisions with electrons, photons, gas molecules, or a surface.

60. The method according to claim 58 wherein the electronic excitation is generated by collisions with electrons, photons, gas molecules, or a surface.

61. The method according to claim 1 wherein the hypothetical biological molecule is generated by a method which comprises:
   a) enzymatically digesting a mixture of biological molecules; and
   b) generating mass data for the biological molecules to generate the hypothetical biological molecule.

62. The method according to claim 1 wherein the score selected in step (e) is from the top ten scores calculated in step (d), wherein the top ten scores denote a high degree of similarity.

63. The method according to claim 1 wherein the score selected in high degree of similarity.

64. The method according to claim 1 wherein the score selected in step (e) is the top score calculated in step (d), wherein the top score denotes a high degree of similarity.

65. The method according to claim 2 wherein the score selected in step (g)(iv) is from the top ten scores calculated in step (g)(iii), wherein the top ten scores denote a high degree of similarity.

66. The method according to claim 2 wherein the score selected in step (g)(iv) is from the top five scores calculated in step (g)(iii), wherein the top five scores denote a high degree of similarity.

67. The method according to claim 2 wherein the score selected in step (g)(iv) is the top score calculated in step (g)(iii), wherein the top score denotes a high degree of similarity.

* * * * *

UNITED STATES PATENT AND TRADEMARK OFFICE
CERTIFICATE OF CORRECTION

PATENT NO. : 6,446,010 B1 Page 1 of 1
DATED : September 3, 2002
INVENTOR(S) : Eriksson et al.

It is certified that error appears in the above-identified patent and that said Letters Patent is hereby corrected as shown below:

Title page,
Item [74], now reads "Hoffman & Baron, LLP;" should read -- Hoffmann & Baron, LLP; --
Item [75], now reads "David Fenyŏ" should read -- David Fenyö --

Column 4,
Line 56, now reads "significance testing a is called" should read -- significance testing $\alpha$ is called --
Line 66, now reads "is shown as $\alpha$" should read -- is shown as a --

Column 9,
Line 1, now reads "$m_i \div \Delta m_i$" should read -- $m_i \pm \Delta m_i$ --

Column 11,
Line 53, now reads "about 300 kDa" should read -- about 3000 kDa --

Column 16,
Line 9, now reads "as: "$\alpha$ protein-identification is…"" should read -- as: "a protein-identification is… --

Column 26,
Line 65, now reads "for em biological" should read -- for biological --

Column 32,
Line 18, now reads "selected in high degree of similarity" should read -- selected in step (e) is from the top five scores calculated in step (d), wherein the top five scores denote a high degree of similarity. --

Signed and Sealed this

Twenty-fifth Day of February, 2003

JAMES E. ROGAN
*Director of the United States Patent and Trademark Office*